US009125922B2

(12) United States Patent
Bennani et al.

(10) Patent No.: US 9,125,922 B2
(45) Date of Patent: *Sep. 8, 2015

(54) PHOSPHATE ESTERS OF GYRASE AND TOPOISOMERASE INHIBITORS

(75) Inventors: Youssef Laafiret Bennani, Lorraine (CA); Paul S. Charifson, Framingham, MA (US); Anne-Laure Grillot, Milton, MA (US); Arnaud Le Tiran, Croissy sur Seine (FR); Hardwin O'Dowd, Boston, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 264 days.

This patent is subject to a terminal disclaimer.

(21) Appl. No.: 13/527,832

(22) Filed: Jun. 20, 2012

(65) Prior Publication Data

US 2013/0157979 A1 Jun. 20, 2013

Related U.S. Application Data

(60) Provisional application No. 61/499,144, filed on Jun. 20, 2011.

(51) Int. Cl.
*A61K 31/685* (2006.01)
*C07D 405/14* (2006.01)
*A61K 31/688* (2006.01)
*A61K 45/06* (2006.01)
*C07F 9/6558* (2006.01)

(52) U.S. Cl.
CPC ............ *A61K 31/685* (2013.01); *A61K 31/688* (2013.01); *A61K 45/06* (2013.01); *C07D 405/14* (2013.01); *C07F 9/65586* (2013.01); *C07B 2200/05* (2013.01)

(58) Field of Classification Search
CPC ............ C07B 2200/05; C07D 405/14; C07F 9/65586; A61K 31/688; A61K 45/06; A61K 31/685
USPC .......................................... 544/243; 514/256
See application file for complete search history.

(56) References Cited

U.S. PATENT DOCUMENTS

| 3,856,957 | A | 12/1974 | Seng et al. |
|---|---|---|---|
| 4,174,400 | A | 11/1979 | Mrozik |
| 4,512,998 | A | 4/1985 | Nafissi-Varchei |
| 5,529,998 | A | 6/1996 | Habich et al. |
| 5,643,935 | A | 7/1997 | Dykstra et al. |
| 6,069,160 | A | 5/2000 | Stolle et al. |
| 6,632,809 | B2 | 10/2003 | Grillot et al. |
| RE40,245 | E | 4/2008 | Grillot et al. |
| 7,414,046 | B2 * | 8/2008 | Grillot et al. ............... 514/215 |
| 7,495,014 | B2 | 2/2009 | Charifson et al. |
| 7,569,591 | B2 | 8/2009 | Charifson et al. |
| 7,582,641 | B2 | 9/2009 | Charifson et al. |
| 7,618,974 | B2 | 11/2009 | Charifson et al. |
| 7,674,801 | B2 | 3/2010 | Basarab et al. |
| 7,727,992 | B2 | 6/2010 | Charifson et al. |
| 7,977,340 | B2 | 7/2011 | Haydon et al. |
| 8,034,832 | B2 | 10/2011 | Charifson et al. |
| 8,067,606 | B2 | 11/2011 | Charifson et al. |
| 8,188,095 | B2 | 5/2012 | Charifson et al. |
| 8,193,352 | B2 | 6/2012 | Charifson et al. |
| 8,404,852 | B2 | 3/2013 | Charifson et al. |
| 8,426,426 | B2 | 4/2013 | Charifson et al. |
| 8,471,014 | B2 | 6/2013 | Shannon et al. |
| 8,476,281 | B2 * | 7/2013 | Shannon et al. ............... 514/256 |
| 8,481,551 | B2 * | 7/2013 | Le Tiran et al. ............... 514/256 |
| 8,481,552 | B2 * | 7/2013 | Shannon et al. ............... 514/256 |
| 2003/0119868 | A1 | 6/2003 | Grillot et al. |
| 2004/0043989 | A1 | 3/2004 | Grillot et al. |
| 2004/0235886 | A1 | 11/2004 | Charifson et al. |
| 2005/0038247 | A1 | 2/2005 | Charifson et al. |
| 2005/0256136 | A1 | 11/2005 | Charifson et al. |
| 2006/0025424 | A1 | 2/2006 | Charifson et al. |
| 2006/0122196 | A9 | 6/2006 | Charifson et al. |
| 2008/0132546 | A1 | 6/2008 | Basarab et al. |
| 2009/0176771 | A1 | 7/2009 | Charifson et al. |
| 2009/0197877 | A1 | 8/2009 | Haydon et al. |
| 2009/0325935 | A1 | 12/2009 | Charifson et al. |
| 2009/0325955 | A1 | 12/2009 | Charifson et al. |
| 2010/0063069 | A1 | 3/2010 | Charifson et al. |
| 2010/0105701 | A1 | 4/2010 | Charifson et al. |
| 2010/0311766 | A1 | 12/2010 | Haydon et al. |
| 2011/0104207 | A1 | 5/2011 | Charifson et al. |
| 2011/0166088 | A1 | 7/2011 | Sattigeri et al. |
| 2011/0263590 | A1 | 10/2011 | Haydon et al. |
| 2012/0004221 | A1 | 1/2012 | Haydon et al. |

(Continued)

FOREIGN PATENT DOCUMENTS

| EP | 0433648 | 6/1991 |
|---|---|---|
| EP | 0738726 | 10/1996 |

(Continued)

OTHER PUBLICATIONS

M. Falagas et al., 40 Clinical Infectious Diseases, 1333-1341 (2005).*
J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
A. Tanitame et al., 47 Journal of Medicinal Chemistry, 3693-3696 (2004).*
S. Alt et al., 66 Journal of Antimicrobial Chemotherapy, 2061-2069 (2011).*
R Bradbury et al., 8 Current Opinion in Pharmacology, 574-581 (2008).*

(Continued)

*Primary Examiner* — Alexander R Pagano
(74) *Attorney, Agent, or Firm* — Brinks Gilson & Lione

(57) ABSTRACT

The present invention relates to phosphate esters of compounds that inhibit bacterial gyrase and/or Topoisomerase IV and pharmaceutical compositions thereof. These phosphate esters are useful for treating bacterial infections.

19 Claims, 1 Drawing Sheet

(56) References Cited

U.S. PATENT DOCUMENTS

| | | | |
|---|---|---|---|
| 2012/0010222 A1 | 1/2012 | Charifson et al. | |
| 2012/0184512 A1 | 7/2012 | Le Tiran et al. | |
| 2012/0184564 A1* | 7/2012 | Shannon et al. | 514/256 |
| 2012/0184741 A1* | 7/2012 | Shannon et al. | 544/333 |
| 2012/0184742 A1* | 7/2012 | Shannon et al. | 544/333 |
| 2013/0157979 A1* | 6/2013 | Bennani et al. | 514/80 |
| 2013/0261305 A1 | 10/2013 | Shannon et al. | |
| 2013/0267540 A1* | 10/2013 | Shannon et al. | 514/256 |
| 2013/0289002 A1 | 10/2013 | Le Tiran et al. | |
| 2013/0317222 A1* | 11/2013 | Shannon et al. | 544/333 |
| 2014/0031318 A1* | 1/2014 | O'Dowd et al. | 514/80 |
| 2014/0045791 A1* | 2/2014 | Locher et al. | 514/80 |

FOREIGN PATENT DOCUMENTS

| | | |
|---|---|---|
| EP | 1055668 | 11/2000 |
| WO | WO 99/35155 | 7/1999 |
| WO | WO 00/49015 | 8/2000 |
| WO | WO 00/71522 | 11/2000 |
| WO | WO 02/060879 | 8/2002 |
| WO | WO 03/105846 | 12/2003 |
| WO | WO 2005/012292 | 10/2005 |
| WO | WO 2006/022773 | 3/2006 |
| WO | WO 2007/056330 | 5/2007 |
| WO | WO 2007/148093 | 12/2007 |
| WO | WO 2008/068470 | 6/2008 |
| WO | WO 2009/074810 | 6/2009 |
| WO | WO 2009/074812 | 6/2009 |
| WO | WO 2009/156966 | 12/2009 |
| WO | WO 2011/032050 | 3/2011 |
| WO | WO 2011/047323 | 4/2011 |
| WO | WO 2012/045124 | 4/2012 |
| WO | WO 2012/097269 | 7/2012 |
| WO | WO 2012/097270 | 7/2012 |
| WO | WO 2012/097273 | 7/2012 |
| WO | WO 2012/177707 | 12/2012 |
| WO | WO 2013/138860 | 9/2013 |

OTHER PUBLICATIONS

Beers, M. H., and Berkow, R., "The Merck Manual of Diagnosis and Therapy", 7th Edition, Chapter 156—Bacteremia and Septic Shock, Merck Research Laboratories, Whitehouse Station, NJ pp. 1143-1147 (1999).
Champoux, J.J., Annu. Rev. Biochem., 2001, 70, pp. 369-413.
Charifson et al., J. Med. Chem., 2008, 51, pp. 5243-5263.
Charles W. Stratton, MD. "In Vitro Susceptibility Testing Versus in Vivo-Effectiveness" The Medical Clinics of North America 2006, 90, 1077-1088.
Drlica and Zhao, Microbiology and Molecular Biology Reviews, 1997, 61, pp. 377-392.
Joseph E. Drumm et al., "Facile preparation of fused ring azolylureas," 48 Tetrahedron Lett. 5535-5538 (2007).
Stephen P. East et al., "DNA gyrase (GyrB)/topoisomerase IV (ParE) inhibitors," 19 Bioorg. Med. Chem. Lett. 894-899 (2009).
Eckert et al., "The antifungal activity of . . . " CA 93:39290 (1980).
Gershman in the Medical Reporter, 1997.
Guven et al. "Synthesis and Antimicrobial Activity of Some Novel Furyl and Benzimidazole Substituted Benzyl Ethers" Journal of Heterocyclic Chemistry 2007, 44, 731.
He et al. "Synthesis and biological evaluation of novel benzimidazoles as potential antibacterial agents." Bioorganic & Medicinal Chemistry Letters 2004, 14, 1217-1220.
Hubschwerlen et al., "Pyrimido[1,6-1]benzimidazoles: A New Class of DNA Gyrase Inhibitors" J. Med. Chem, vol. 35, No. 8, pp. 1385-1392, 1992.

International Search Report and Written Opinion of the International Searching Authority, International Patent Application No. PCT/US2012/021270 (Mar. 16, 2012).
International Search Report and Written Opinion of the International Searching Authority, International Patent Application No. PCT/US2012/021281 (May 3, 2012).
International Search Report and Written Opinion of the International Searching Authority, International Patent Application No. PCT/US2012/021280 (Mar. 23, 2012).
International Search Report and Written Opinion of the International Searching Authority, International Patent Application No. PCT/US2012/021275 (Mar. 23, 2012).
International Search Report and Written Opinion of the International Searching Authority, International Patent Application No. PCT/US2012/043266 (Aug. 28, 2012).
International Search Report and Written Opinion of the International Searching Authority, International Patent Application No. PCT/US2012/051008 (Oct. 14, 2013).
International Search Report and Written Opinion of the International Searching Authority, International Patent Application No. PCT/US2012/050564 (Oct. 8, 2013).
Kornberg and Baker, DNA Replication, 2d Ed., Chapter 12, 1992, W. H. Freeman and Co.
Kus, C., "Synthesis and Antimicrobial Activities of 5-fluoro-1, 2, 6-trisubstituted benzimidazole carboxamide and acetamide derivatives," Arch. Pharm. Pharm. Med. Chem. 334(11):361-365 (2001).
Levy, "The Challenge of Antibiotic Resistance", Scientific American, Mar. 1998).
Lewis, "The Rise of Antibiotic-Resistant Infections", FDA Consumer magazine, Sep. 1995.
Maxwell, Mol. Microbiol., 1993, 9, 681.
Maxwell, Trends in Microbiology, 1997, 5, 102.
MayoClinic "Antibiotic associated diarrhea" Mayoclinic.com. (2007).
Nicolaus B.J.R., "Symbiotic Approach to Drug Design," Decision Making in Drug Research, pp. 173-186 (1983).
Pea et al., PubMed Abstract (Clin Pharmacokinet. 44(10):1009-34) 2005.
Singh, S.K., et al., "Studies in antiparastic agents: Part 13—Synthtesis of 4-aryl-2-substitutedamino-thiazoles as potential anthelmintics," Indian J. Chem., 28B (9):786-789 (1989).
Skopenka, V.V., et al., "Organotin Carbamoyldicyanomethanide, nitrosocarbamoylcyanomethanide, and Carbamoylcyanides," retrieved from STN Database accession No. 101:230674, XP002254350 abstract and Dopovidi Akademii Nauk Ukrains'Koi RSR, Seriya B: Geologichni, Khimichni Ta Biologichni Nauki, 7:44-46 (1984).
Snyder et al., PubMed Abstract (J. Med Liban. 48(4):208-14), Jul.-Aug. 2000.
Sun et al., "Synthesis and Evaluation of Terbenzimidazoles as Topoisomerase I Inhibitors" J. Med. Chem., vol. 38, No. 18, pp. 3638-3644, 1995.
Tanitame et al. "Design, synthesis and structure-activity relationship studies of novel indazole analogues as DNA gyrase inhibitors with Gram-positive antibacterial activity" Bioorganic & Medicinal Chemistry Letters 2004, 14, 2857-2862.
Drlica, Molecular Microbiology, 1992, 6, 425.
Wassenaar "Bacteria; more than pathogens" Am. Ins. Biol. Sci. Internet p. 1-7 (2002).
Webster's Dictionary (1984) p. 933.
WHO Report, "Use of Quinolones in Food Animals and Potential Impact on Human Health", 1998.
Matthew E. Falagas et al., "Colistin: The Revival of Polymyxins for the Management of Multidrug-Resistant Gram-Negative Bacterial Infections," *Reviews of Anti-Infective Agents*, CID 2005:40 (2005), pp. 1333-1341.

* cited by examiner

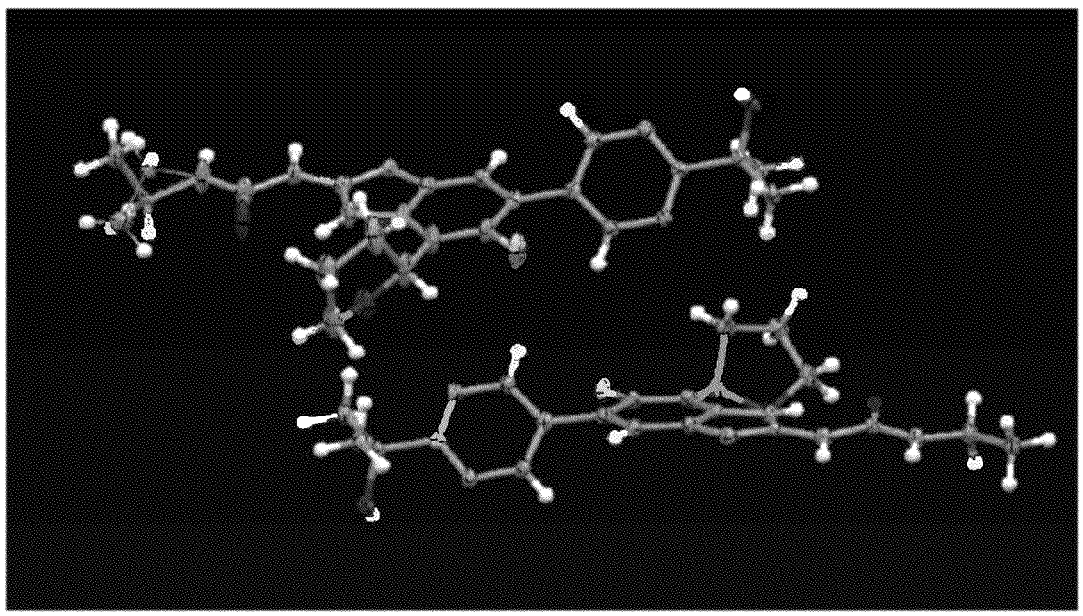

PHOSPHATE ESTERS OF GYRASE AND TOPOISOMERASE INHIBITORS

CROSS REFERENCE TO RELATED APPLICATIONS

This application claims the benefit under 35 U.S.C. §119 of U.S. Provisional Patent Application Ser. No. 61/499,144 filed Jun. 20, 2011; the entire contents of which are incorporated herein by reference.

BACKGROUND OF THE INVENTION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *Mycobacterium tuberculosis*, and *Enterococcus*. The appearance of Vancomycin resistant *enterococcus* was particularly alarming because Vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., Current Opinion in Anti-infective Investigational Drugs, 1999, 1, 1; Levy, "The Challenge of Antibiotic Resistance", Scientific American, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in The Medical Reporter, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", FDA Consumer magazine, September 1995).

As a result of the need to combat drug-resistant bacteria and the increasing failure of the available drugs, there has been a resurgent interest in discovering new antibiotics. One attractive strategy for developing new antibiotics is to inhibit DNA gyrase and/or topoisomerase IV, bacterial enzymes necessary for DNA replication, and therefore, necessary for bacterial cell growth and division. Gyrase and/or topoisomerase IV activity are also associated with events in DNA transcription, repair and recombination.

Gyrase is one of the topoisomerases, a group of enzymes which catalyze the interconversion of topological isomers of DNA (see generally, Kornberg and Baker, DNA Replication, 2d Ed., Chapter 12, 1992, W. H. Freeman and Co.; Drlica, Molecular Microbiology, 1992, 6, 425; Drlica and Zhao, Microbiology and Molecular Biology Reviews, 1997, 61, pp. 377-392). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase and/or topoisomerase IV would be selective for these enzymes and be relatively inactive against the eukaryotic type II topoisomerases.

Topoisomerase IV primarily resolves linked chromosome dimers at the conclusion of DNA replication.

The widely-used quinolone antibiotics inhibit bacterial DNA gyrase (GyrA) and/or Topoisomerase IV (ParC). Examples of the quinolones include the early compounds such as nalidixic acid and oxolinic acid, as well as the later, more potent fluoroquinolones such as norfloxacin, ciprofloxacin, and trovafloxacin. These compounds bind to GyrA and/or ParC and stabilize the cleaved complex, thus inhibiting overall gyrase function, leading to cell death. The fluoroquinolones inhibit the catalytic subunits of gyrase (GyrA) and/or Topoisomerase IV (Par C) (see Drlica and Zhao, Microbiology and Molecular Biology Reviews, 1997, 61, 377-392). However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

The associated subunits responsible for supplying the energy necessary for catalytic turnover/resetting of the enzymes via ATP hydrolysis are GyrB (gyrase) and ParE (topoisomerase IV), respectively (see, Champoux, J. J., Annu. Rev. Biochem., 2001, 70, pp. 369-413). Compounds that target these same ATP binding sites in the GyrB and ParE subunits would be useful for treating various bacterial infections (see, Charifson et al., J. Med. Chem., 2008, 51, pp. 5243-5263).

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, Trends in Microbiology, 1997, 5, 102).

For coumarin-resistant bacteria, the most prevalent point mutation is at a surface arginine residue that binds to the carbonyl of the coumarin ring (Arg136 in *E. coli* GyrB). While enzymes with this mutation show lower supercoiling and ATPase activity, they are also less sensitive to inhibition by coumarin drugs (Maxwell, Mol. Microbiol., 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, Trends in Microbiology, 1997, 5, 102). It would be desirable to have a new, effective GyrB and ParE inhibitor that overcomes these drawbacks and, preferably does not rely on binding to Arg136 for activity. Such an inhibitor would be an attractive antibiotic candidate, without a history of resistance problems that plague other classes of antibiotics.

As bacterial resistance to antibiotics has become an important public health problem, there is a continuing need to develop newer and more potent antibiotics. More particularly, there is a need for antibiotics that represent a new class of compounds not previously used to treat bacterial infection. Compounds that target the ATP binding sites in both the GyrB (gyrase) and ParE (topoisomerase IV) subunits would be useful for treating various bacterial infections. Such compounds would be particularly useful in treating nosocomial infections in hospitals where the formation and transmission of resistant bacteria are becoming increasingly prevalent. Furthermore, there is a need for new antibiotics having a broad spectrum of activity with advantageous toxicological properties.

SUMMARY OF THE INVENTION

The present invention is directed to compounds and pharmaceutically acceptable salts thereof, compositions, useful as gyrase and/or topoisomerase IV inhibitors. The gyrase and/or topoisomerase IV inhibitors of the present invention may be represented by formula (I) or salts thereof:

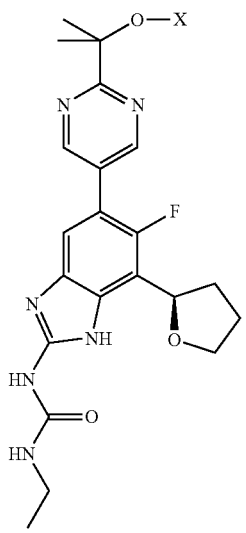

(I)

wherein X is $-PO(OH)O-R^1$, or $-PO(O^-M^+)O-R^1$; $M^+$ is a pharmaceutically acceptable monovalent cation; $R^1$ is $(C_1-C_{20})$-alkyl, $(C_2-C_{20})$-alkenyl, $-(CH_2CH_2O)_nCH_3$, or $R^2$; wherein said alkyl or alkenyl is optionally substituted with $R^2$, $-OR^9$, $-N(R^9)_2$, $-CN$, $-C(O)OR^9$, $-C(O)N(R^9)_2$, $-N(R^9)-C(O)-R^9$, halogen, $-CF_3$, or $-NO_2$; each $R^2$ is independently a 5-6 membered carbocyclic or heterocyclic aliphatic ring system; wherein any of said heterocyclic ring systems contains one or more heteroatoms selected from O, N, and $N(R^9)$; and wherein any of said ring systems optionally contains 1 to 4 substituents independently selected from $-OH$, $C_1-C_4$ alkyl, and $-O-(C_1-C_4)$-alkyl; each $R^9$ is independently H or a $C_1-C_4$ alkyl group; and n is an integer 1 to 5. The compounds of formula (I) are phosphate ester prodrugs of the compound (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, which possesses a broad range of anti-bacterial activity and advantageous toxicological properties.

In addition to the compounds provided herein, the present invention further provides a pharmaceutical composition comprising a compound of formula (I) or a pharmaceutically acceptable salt thereof and a pharmaceutically acceptable carrier, adjuvant, or vehicle.

In another embodiment, the present invention relates to a pharmaceutical composition comprising a compound of formula (I) or a pharmaceutically acceptable salt thereof; a pharmaceutically acceptable carrier, adjuvant, or vehicle; and an additional therapeutic agent selected from an antibiotic, an anti-inflammatory agent, a matrix metalloproteinase inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

In another embodiment, the present invention relates to a method of controlling, treating or reducing the advancement, severity or effects of a bacterial infection in a patient, comprising administering to said patient a therapeutically effective amount of a compound of formula (I) or a pharmaceutically acceptable salt thereof.

In a further embodiment, the present invention relates to a method of controlling, treating or reducing the advancement, severity or effects of a bacterial infection in a patient, comprising administering to said patient a therapeutically effective amount of a compound of formula (I) or a pharmaceutically acceptable salt thereof and an antibiotic, an anti-inflammatory agent, a matrix metalloproteinase inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound, either as part of a multiple dosage form together with said compound or as a separate dosage form.

In another embodiment, the present invention relates to a method of preventing, controlling, treating, or reducing the advancement, severity or effects of a bacterial infection in a mammal, comprising administering to said mammal a therapeutically effective amount of a compound of formula (I) or a pharmaceutically acceptable salt thereof.

BRIEF DESCRIPTION OF THE DRAWING

FIG. 1 is a thermal ellipsoid plot of two symmetry independent molecules of compound 23.

DETAILED DESCRIPTION OF THE INVENTION

The instant compounds are prodrugs of their parent compound, (R)-1-ethyl-3-(6-fluoro-5-(2-(2-hydroxypropan-2- yl)pyrimidin-5-yl)-7-(tetrahydrofuran-2-yl)-1H-benzo[d]imidazol-2-yl)urea. Thus, the activity exhibited upon administration of the prodrug is principally due to the presence of the parent compound that results from cleavage of the prodrug.

The term "prodrug" refers to compounds which are drug precursors which, following administration and absorption, release the drug in vivo via some metabolic process. In general, a prodrug possesses less biological activity than its parent drug. A prodrug may also improve the physical properties of the parent drug and/or it may also improve overall drug efficacy, for example through the reduction of toxicity and unwanted effects of a drug by controlling its absorption, blood levels, metabolic distribution and cellular uptake.

The term "parent compound" or "parent drug" refers to the biologically active entity that is released via enzymatic action of a metabolic or a catabolic process, or via a chemical process following administration of the prodrug. The parent compound may also be the starting material for the preparation of its corresponding prodrug.

The monovalent cations defined by M$^+$ include ammonium, alkali metal ions such as sodium, lithium and potassium ions, dicyclohexylamine ion, and N-methyl-D-glucamine ion. Also included are amino acid cations such as ions of arginine, lysine, ornithine, and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "alkyl", used alone or as part of a larger moiety refers to a hydrocarbon group which may be linear or branched and having the number of carbon atoms designated (i.e. "($C_1$-$C_{20}$)" means one to twenty carbons, "($C_1$-$C_4$)" or "$C_1$-$C_4$" means one to four carbons, etc.). The term "alkenyl" used alone or as part of a larger moiety refers to an unsaturated hydrocarbon group which may be linear or branched and having the number of carbon atoms designated (i.e. "($C_1$-$C_{20}$)" means one to twenty carbons, "($C_1$-$C_4$)" or "$C_1$-$C_4$" means one to four carbons, etc.).

The term "halo" or "halogen", by itself or as part of a substituent refers to fluorine, chlorine, bromine and iodine atom.

The term "carbocycle", as used herein, means a cyclic hydrocarbon group that is completely saturated or that contains one or more units of unsaturation, that has a single point of attachment to the rest of the molecule. The term "5-6 membered carbocyclic" refers to a $C_5$ or $C_6$ cyclic alkyl group that is completely saturated or contains one or more units of unsaturation, but which is not aromatic. Suitable ""5-6 membered carbocyclic" groups include cyclopentyl, cyclohexyl, cyclopentenyl, cyclohexenyl, cyclopentylmethyl, and the like.

The term "heterocycle", "heterocyclic", "heterocyclyl", or "heterocyclic aliphatic ring system" refers to a saturated or unsaturated non-aromatic ring containing at least one heteroatom (typically 1 to 4 heteroatoms) selected from nitrogen, oxygen or sulfur. Preferably, these groups contain 0-4 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, piperidine, 1,4-dioxane, morpholine, thiomorpholine, thiomorpholine-S-oxide, thiomorpholine-S, S-dioxide, piperazine, pyran, pyridone, 3-pyrroline, thiopyran, pyrone, tetrahydrofuran, tetrahydrothiophene, and the like.

Isotopically-labeled forms of compounds of formula (I) wherein one or more atoms are replaced by an atom having an atomic mass or mass number different from the atomic mass or mass number usually found in nature are also included herein. Examples of isotopes that can be incorporated into compounds of the invention include isotopes of hydrogen, carbon, nitrogen, oxygen, and fluorine, such as $^2$H, $^3$H, $^{13}$C, $^{14}$C, $^{15}$N, $^{18}$O, and $^{17}$O. Such radio-labeled and stable-isotopically labeled compounds are useful, for example, as research or diagnostic tools or gyrase and/or topoisomerase IV inhibitors with improved therapeutic profile. The structures also encompass zwitterionic forms of the compounds or salts, where appropriate.

Various embodiments of the invention, include compounds or salts of formula (I) as set forth below:
(1) compounds wherein X is
 (a) —PO(OH)O—R$^1$; or
 (b) —PO(O$^-$M$^+$)O—R$^1$;
(2) compounds wherein M$^+$ is
 (a) Li$^+$, Na$^+$, K$^+$, N-methyl-D-glucamine, or N(R$^9$)$_4$$^+$; or
 (b) Na$^+$ or NH$_4$$^+$;
(3) compounds wherein R$^1$ is
 (a) ($C_1$-$C_{20}$)-alkyl, ($C_2$-$C_{20}$)-alkenyl, or —O(CH$_2$CH$_2$O)$_n$CH$_3$, wherein n is an integer 1, 2 or 3, morpholinoethyl, 4-ethyltetrahydro-2H-pyranyl, piperidinylethyl, piperazinylethyl, or pyrrolidinylethyl;
 (b) morpholinoethyl, 4-ethyltetrahydro-2H-pyranyl, piperidinylethyl, piperazinylethyl, or pyrrolidinylethyl;
 (c) ($C_1$-$C_{20}$)-alkyl; or
 (d) —O(CH$_2$CH$_2$O)$_n$CH$_3$, wherein n is an integer 1, 2 or 3;
(4) (R)-2-(5-(2-(3-ethylureido)-6-fluoro-7-(tetrahydrofuran-2-yl)-1H-benzo[d]imidazol-5-yl)pyrimidin-2-yl)propan-2-yl 2-(2-methoxyethoxy)ethyl hydrogen phosphate;
(5) ammonium(R)-2-(5-(2-(3-ethylureido)-6-fluoro-7-(tetrahydrofuran-2-yl)-1H-benzo[d]imidazol-5-yl)pyrimidin-2-yl)propan-2-yl 2-(2-methoxyethoxy)ethyl phosphate;
(6) (R)-2-(5-(2-(3-ethylureido)-6-fluoro-7-(tetrahydrofuran-2-yl)-1H-benzo[d]imidazol-5-yl)pyrimidin-2-yl)propan-2-yl hexadecyl hydrogen phosphate;
(7) ammonium (R)-2-(5-(2-(3-ethylureido)-6-fluoro-7-(tetrahydrofuran-2-yl)-1H-benzo[d]imidazol-5-yl)pyrimidin-2-yl)propan-2-yl hexadecyl phosphate; and
(8) 2-(5-(2-(3-ethylureido)-6-fluoro-7-((R)-tetrahydrofuran-2-yl)-1H-benzo[d]imidazol-5-yl)pyrimidin-2-yl)propan-2-yl 2-morpholinoethyl hydrogen phosphate.

It is understood that various alternative embodiments of the compounds or salts of formula (I) can be selected by requiring one or more of the alternate embodiments listed in (1) through (3) above. For example, further embodiments of the invention can be obtained by combining (1)(a) and (3)(a); (1)(a) and (3)(b); (1)(a) and (3)(c); (1)(a) and (3)(d); (1)(b), (2)(a), and (3)(a); (1)(b), (2)(a), and (3)(b); (1)(b), (2)(a), and (3)(c); (1)(b), (2)(a), and (3)(d); (1)(b), (2)(b), and (3)(a); (1)(b), (2)(b), and (3)(b); (1)(b), (2)(b), and (3)(c); (1)(b), (2)(b), and (3)(d); and the like.

The prodrugs of the present invention are characterized by unexpectedly high aqueous solubility. This solubility facilitates administration of higher doses of the prodrug, resulting in a greater drug load per unit dosage.

One embodiment of this invention relates to a method of controlling, treating or reducing the advancement, severity or effects of a bacterial infection in a patient, comprising administering to said patient a therapeutically effective amount of a compound having the formula (I) or a pharmaceutically acceptable salt thereof.

According to another embodiment, the invention provides a method of decreasing or inhibiting bacterial quantity in a biological sample. This method comprises contacting said biological sample with a compound of formula (I) or a pharmaceutically acceptable salt thereof.

The term "biological sample", as used herein, includes cell cultures or extracts thereof; biopsied material obtained from a mammal or extracts thereof; and blood, saliva, urine, feces, semen, tears, or other body fluids or extracts thereof. The term "biological sample" also includes living organisms, in which case "contacting a compound of this invention with a biological sample" is synonymous with the term "administrating said compound for composition comprising said compound) to a mammal".

One embodiment comprises contacting said biological sample with a phosphate ester prodrug of (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, as defined by formula (I). Pharmaceutical compositions useful for such methods are described below.

The gyrase and/or topoisomerase IV inhibitors of this invention, or pharmaceutical salts thereof, may be formulated into pharmaceutical compositions for administration to animals or humans. These pharmaceutical compositions effective to treat or prevent a bacterial infection which comprise the gyrase and/or topoisomerase IV inhibitor in an amount sufficient to measurably decrease bacterial quantity and a pharmaceutically acceptable carrier, adjuvant, or vehicle are another embodiment of the present invention. The term "measurably decrease bacterial quantity", as used herein means a measurable change in the number of bacteria between a sample containing said inhibitor and a sample containing only bacteria.

Agents which increase the susceptibility of bacterial organisms to antibiotics are known. For example, U.S. Pat. No. 5,523,288, U.S. Pat. No. 5,783,561 and U.S. Pat. No. 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in Microbiological Reviews (1992) pp. 395-411, and the sensitization of gram-negative bacteria has been described by Tsubery, H., et al, in J. Med. Chem. (2000) pp. 3085-3092.

Another embodiment of this invention relates to a method, as described above, of controlling, treating or reducing the advancement, severity or effects of a bacterial infection in a patient, but further comprising the step of administering to said patient an agent which increases the susceptibility of bacterial organisms to antibiotics.

According to another embodiment, the methods of the present invention are useful to treat patients in the veterinarian field including, but not limited to, zoo, laboratory, human companion, and farm animals including primates, rodents, reptiles and birds. Examples of said animals include, but are not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, ostriches, chickens, turkeys, ducks, and geese.

According to another embodiment, the present invention provides a method of decreasing or inhibiting *Streptococcus pneumoniae, Staphylococcus epidermidis, Enterococcus faecalis, Enterococcus faecium, Staphylococcus aureus, Clostridium difficile, Moraxella catarrhalis, Neisseria gonorrhoeae, Neisseria meningitidis, Mycobacterium tuberculosis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci bacterial quantity in a biological sample comprising contacting said biological sample with the compound of formula (I), or a pharmaceutically acceptable salt thereof.

The pharmaceutical compositions and methods of this invention will be useful generally for controlling bacterial infections in vivo. Examples of bacterial organisms that may be controlled by the compositions and methods of this invention include, but are not limited to the following organisms: *Streptococcus pneumoniae, Streptococcus pyogenes, Enterococcus faecalis, Enterococcus faecium, Klebsiella pneumoniae, Enterobacter* spp. *Proteus* spp. *Pseudomonas aeruginosa, E. coli, Serratia marcescens, Staphylococcus aureus,* Coag. Neg. Staphylococci, *Haemophilus influenzae, Bacillus anthracis, Mycoplasma pneumoniae, Moraxella catarrhalis, Chlamydophila pneumoniae, Chlamydia trachomatis, Legionella pneumophila, Mycobacterium tuberculosis, Helicobacter pylori, Staphylococcus saprophyticus, Staphylococcus epidermidis, Francisella tularensis, Yersinia pestis, Clostridium difficile, Neisseria gonorrhoeae, Neisseria meningitidis, Mycobacterium avium* complex, *Mycobacterium abscessus, Mycobacterium kansasii* and *Mycobacterium ulcerans.*

The compositions and methods will therefore be useful for controlling, treating or reducing the advancement, severity or effects of nosocomial or non-nosocomial infections. Examples of nosocomial and non-nosocomial infections include but are not limited to upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections. Examples of specific bacterial infections include but are not limited to uncomplicated skin and skin structure infections, complicated skin and skin structure infections (cSSSI), catheter infections, pharyngitis, sinusitis, otitis externa, otitis media, bronchitis, empyema, pneumonia, community acquired pneumoniae (CAP), hospitalized acquired pneumonia, hospitalized bacterial pneumonia, diabetic foot infections, vancomycin resistant enterococci infections, cystitis and pyelonephritis, renal calculi, prostatitis, peritonitis and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

The term "non-nosocomial infections" is also referred to as community acquired infections.

In one embodiment, the compositions and methods will therefore be useful for controlling, treating or reducing the advancement, severity or effects of community acquired pneumoniae (CAP), hospitalized acquired pneumonia, hospitalized bacterial pneumonia, bacteremia, diabetic foot infections, catheter infections, uncomplicated skin and skin structure infections, complicated skin and skin structure infections (cSSSI), Vancomycin resistant enterococci infections or osteomyelitis.

In another embodiment, the compositions and methods will therefore be useful for controlling, treating or reducing the advancement, severity or effects of upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections, uncomplicated skin and skin structure infections, complicated skin and skin structure infections (cSSSI), catheter infections, pharyngitis, sinusitis, otitis externa, otitis media, bronchitis, empyema, pneumonia, community acquired pneumoniae (CAP), hospitalized acquired pneumonia, hospitalized bacterial pneumonia, diabetic foot infections, Vancomycin resistant enterococci infections, cystitis and pyelonephritis, renal calculi, prostatitis, peritonitis and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

In another embodiment, the bacterial infection is characterized by the presence of one or more of *Streptococcus pneumoniae, Streptococcus pyogenes, Enterococcus faecalis, Enterococcus faecium, Staphylococcus aureus*, Coag. Neg. Staphlococci, *Bacillus anthracis, Staphylococcus epidermidis, Staphylococcus saprophyticus*, or *Mycobacterium tuberculosis*.

In another embodiment, the bacterial infection is characterized by the presence of one or more of *Streptococcus pneumoniae, Enterococcus faecalis*, or *Staphylococcus aureus*.

In another embodiment, the bacterial infection is characterized by the presence of one or more of *E. coli, Moraxella catarrhalis*, or *Haemophilus influenzae*.

In another embodiment, the bacterial infection is characterized by the presence of one or more of *Clostridium difficile, Neisseria gonorrhoeae, Neisseria meningitidis, Mycobacterium tuberculosis, Mycobacterium avium* complex, *Mycobacterium abscessus, Mycobacterium kansasii, Mycobacterium ulcerans, Chlamydophila pneumoniae* and *Chlamydia tracomatis*.

In another embodiment, the bacterial infection is characterized by the presence of one or more of *Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium tuberculosis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci.

In some embodiments, the bacterial infection is characterized by the presence of one or more of Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant Coagulase negative *staphylcoccus*, Fluoroquinolone resistant Coagulase negative *staphylcoccus*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, δ-lactam resistant *Enterococcus faecium*, Ketolide resistant *Streptococcus pneumoniae*, Ketolide resistant *Streptococcus pyogenes*, Macrolide resistant *Streptococcus pyogenes*, Vancomycin resistant *staphylococcus epidermidis*, Fluoroquinolone resistant *Neisseria gonorrhoeae*, Multidrug Resistant *Pseudomonas aeruginosa* or Cephalosporin resistant *Neisseria gonorrhoeae*.

According to another embodiment, the Methicillin resistant Staphylococci are selected from Methicillin resistant *Staphylococcus aureus*, Methicillin resistant *Staphylococcus epidermidis*, or Methicillin resistant Coagulase negative *staphylcoccus*.

In some embodiments, a form of a compound of formula (I) is used to treat community acquired MRSA (i.e., cMRSA).

In other embodiments, a form of a compound of formula (I) is used to treat daptomycin resistant organism including, but not limited to, daptomycin resistant *Enterococcus faecium* and daptomycin resistant *Staphylococcus aureus*.

According to another embodiment, the Fluoroquinolone resistant Staphylococci are selected from Fluoroquinolone resistant *Staphylococcus aureus*, Fluoroquinolone resistant *Staphylococcus epidermidis*, or Fluoroquinolone resistant Coagulase negative *staphylcoccus*.

According to another embodiment, the Glycopeptide resistant Staphylococci are selected from Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, or Hetero vancomycin resistant *Staphylococcus aureus*.

According to another embodiment, the Macrolide-Lincosamide-Streptogramin resistant Staphylococci is Macrolide-Lincosamide-Streptogramin resistant *Staphylococcus aureus*.

According to another embodiment, the Linezolid resistant Enterococci are selected from Linezolid resistant *Enterococcus faecalis*, or Linezolid resistant *Enterococcus faecium*.

According to another embodiment, the Glycopeptide resistant Enterococci are selected from Vancomycin resistant *Enterococcus faecium* or Vancomycin resistant *Enterococcus faecalis*.

According to another embodiment, the β-lactam resistant *Enterococcus faecalisis* β-lactam resistant *Enterococcus faecium*.

According to another embodiment, the Penicillin resistant Streptococci is Penicillin resistant *Streptococcus pneumoniae*.

According to another embodiment, the Macrolide resistant Streptococci is Macrolide resistant *Streptococcus pneumonia*.

According to another embodiment, the Ketolide resistant Streptococci are selected from Macrolide resistant *Streptococcus pneumoniae* and Ketolide resistant *Streptococcus pyogenes*.

According to another embodiment, the Fluoroquinolone resistant Streptococci is Fluoroquinolone resistant *Streptococcus pneumoniae*.

According to another embodiment, the β-lactam resistant *Haemophilus* is β-lactam resistant *Haemophilus influenzae*.

According to another embodiment, the Fluoroquinolone resistant *Haemophilus* is Fluoroquinolone resistant *Haemophilus influenzae*.

According to another embodiment, the Macrolide resistant *Haemophilus* is Macrolide resistant *Haemophilus influenzae*.

According to another embodiment, the Macrolide resistant *Mycoplasma* is Macrolide resistant *Mycoplasma pneumoniae*.

According to another embodiment, the Isoniazid resistant *Mycobacterium* is Isoniazid resistant *Mycobacterium tuberculosis*.

According to another embodiment, the Rifampin resistant *Mycobacterium* is Rifampin resistant *Mycobacterium tuberculosis*.

According to another embodiment, the β-lactam resistant *Moraxella* is β-lactam resistant *Moraxella catarrhalis*.

According to another embodiment, the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Fluoroquinolone resistant *Neisseria gonorrhoeae* or Cephalosporin resistant *Neisseria gonorrhoeae*.

According to another embodiment, the bacterial infection is characterized by the presence of one or more of the following: Methicillin resistant *Staphylococcus aureus*, Methicillin resistant *Staphylococcus epidermidis*, Methicillin resistant Coagulase negative *staphylcoccus*, Fluoroquinolone resistant *Staphylococcus aureus*, Fluoroquinolone resistant *Staphylococcus epidermidis*, Fluoroquinolone resistant Coagulase negative *staphylcoccus*, Vancomycin resistant *Staphylococcus aureus*, Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Vancomycin resistant *Enterococcus faecium*, Vancomycin resistant *Enterococcus faecalis*, Penicillin resistant *Streptococcus pneumoniae*, Macrolide resistant *Streptococcus pneumoniae*, Fluoroquinolone resistant *Streptococcus pneumoniae*, Macrolide resistant *Streptococcus pyogenes*, or β-lactam resistant *Haemophilus influenzae*.

According to another embodiment, the bacterial infection is characterized by the presence of one or more of the following: Methicillin resistant *Staphylococcus aureus*, Vancomycin resistant *Enterococcus faecium*, Vancomycin resistant *Enterococcus faecalis*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Multidrug Resistant *Pseudomonas aeruginosa*, Isoniazid resistant *Mycobacterium tuberculosis*, or Rifampin resistant *Mycobacterium tuberculosis*.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

Pharmaceutical compositions of this invention comprise a compound of formula (I) or a pharmaceutically acceptable salt thereof and a pharmaceutically acceptable carrier. Such compositions may optionally comprise an additional therapeutic agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an antiviral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as alpha-tocopherol, polyethyleneglycol 1000 succinate, or other similar polymeric delivery matrices.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

Depending upon the particular condition, or disease state, to be treated or prevented, additional therapeutic agents, which are normally administered to treat or prevent that condition, may be administered together with the inhibitors of this invention. Such therapeutic agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immuno-modulator, a prostaglandin or an anti-vascular hyperproliferation compound.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

In some embodiments, compounds of formula (I) may be used prophylactically to prevent a bacterial infection. In some embodiments, compounds of formula (I) may be used before, during or after a dental or surgical procedure to prevent opportunistic infections such as those encountered in bacterial endocarditis. In other embodiments, compounds of formula (I) may be used prophylactically in dental procedures, including but not limited to extractions, periodontal procedures, dental implant placements and endodontic surgery. In other embodiments, compounds of formula (I) may be used prophylactically in surgical procedures including but not limited to general surgery, respiratory surgery (tonsillectomy/adenoidectomy), gastrointestinal surgery (upper GI and elective small bowel surgery, esophageal sclerotherapy and dilation, large bowel resections, acute appendectomy), trauma surgery (penetrating abdominal surgery), genito-urinary tract surgery (prostatectomy, urethral dilation, cystoscopy, vaginal or abdominal hysterectomy, cesarean section), transplant surgery (kidney, liver, pancreas or kidney transplantation), head and neck surgery (skin excisions, neck dissections, laryngectomy, head and neck cancer surgeries, mandibular fractures), orthopaedic surgery (total joint replacement, traumatic open fractures), vascular surgery (peripheral vascular procedures), cardiothoracic surgery, coronary bypass surgery, pulmonary resection and neurosurgery.

The term "prevent a bacterial infection" as used herein, unless otherwise indicated, means the prophylatic use of an antibiotic, such as a gyrase and/or topoisomerase IV inhibitor of the present invention, to prevent a bacterial infection. Treatment with a gyrase and/or topoisomerase IV inhibitor could be done prophylactically to prevent an infection caused by an organism that is susceptible to the gyrase and/or topoisomerase IV inhibitor. One general set of conditions where prophylactic treatment could be considered is when an individual is more vulnerable to infection due to, for example, weakened immunity, surgery, trauma, presence of an artificial device in the body (temporary or permanent), an anatomical defect, exposure to high levels of bacteria or possible exposure to a disease-causing pathogen. Examples of factors that could lead to weakened immunity include chemotherapy, radiation therapy, diabetes, advanced age, HIV infection, and transplantation. An example of an anatomical defect would be a defect in the heart valve that increases the risk of bacterial endocarditis. Examples of artificial devices include artificial joints, surgical pins, catheters, etc. Another set of situations where prophylactic use of a gyrase and/or topoisomerase IV inhibitor might be appropriate would be to prevent the spread of a pathogen between individuals (direct or indirect). A specific example of prophylactic use to prevent the spread of a pathogen is the use of a gyrase and/or topoisomerase IV inhibitor by individuals in a healthcare institution (for example a hospital or nursing home).

The compounds of formula (I) may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula (I) and another therapeutic or prophylactic agent.

In some embodiments, the additional therapeutic agent or agents is an antibiotic selected from a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide.

In some embodiments, the additional therapeutic agent or agents is an antibiotic selected from a penicillin, a cephalosporin, a quinolone, an aminoglycoside or an oxazolidinone.

In other embodiments, the additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/ tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, Ceftaroline and Ceftobiprole, from a Cephamycin including Cefotetan and Cefoxitin, from a carbapenem including Doripenem, Imipenem and Meropenem, from a monobactam including Aztreonam, from a quinolone including Cinoxacin, Nalidixic acid, Oxolininc acid and Pipemidic acid, from a fluoroquinolone including Besifloxacin, Ciprofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Dalbavancin, Telavancin, Teicoplanin and Vancomycin, from a streptogramin including Dalfopristin/quinupristin, from an oxazolidone including Linezolid, from a Rifamycin including Rifabutin and Rifampin and from other antibiotics including bactitracin, colistin, Tygacil, Daptomycin, chloramphenicol, clindamycin, isoniazid, metronidazole, mupirocin, polymyxin B, pyrazinamide, trimethoprim/sulfamethoxazole and sulfisoxazole.

In other embodiments, the additional therapeutic agents are selected from a natural penicillin including Penicillin G, from a penicillinase-resistant penicillin including Nafcillin and Oxacillin, from an antipseudomonal penicillin including Pipercillin/tazobactam, from an aminopenicillin including Amoxicillin, from a first generation cephalosporin including Cephalexin, from a second generation cephalosporin including Cefaclor, Cefaclor-CD and Cefuroxime, from a third generation cephalosporin including Ceftazidime and Ceftriaxone, from a fourth generation cephalosporin including Cefepime, from a carbapenem including Imepenem, Meropenem, Ertapenem, Doripenem, Panipenem and Biapenem, a fluoroquinolone including Ciprofloxacin, Gatifloxacin, Levofloxacin and Moxifloxacin, from an aminoglycoside including Tobramycin, from a macrolide including Azithromycin and Clarithromycin, from a Tetracycline including Doxycycline, from a glycopeptide including Vancomycin, from a Rifamycin including Rifampin and from other antibiotics including isoniazid, pyrazinamide, Tygacil, Daptomycin or trimethoprim/sulfamethoxazole.

In some embodiments, a solid form of a compound of formula (I), can be administered for the treatment of a gram positive infection. In some embodiments, the composition is a solid, liquid (e.g., a suspension), or an iv (e.g., a form of the formula (I) compound is dissolved into a liquid and administered iv) composition. In some embodiments, the composition including a formula (I) compound, is administered in combination with an additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide. In some embodiments, the composition including a solid form of a formula (I) compound is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide is administered iv.

In some embodiments, a solid form of a formula (I) compound, can be administered for the treatment of a gram negative infection. In some embodiments, the composition is a solid, liquid (e.g., a suspension), or an iv (e.g., a form of a formula (I) compound is dissolved into a liquid and administered iv) composition. In some embodiments the composition including a formula (I) compound is administered in combination with an additional antibiotic agent, selected from a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a polymyxin, tetracycline or a sulfonamide. In some embodiments, the composition including a solid form of a formula (I) compound is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a polymyxin, tetracycline or a sulfonamide is administered orally. In some embodiments, the additional therapeutic agent is administered iv.

The additional therapeutic agents described above may be administered separately, as part of a multiple dosage regimen, from the inhibitor-containing composition. Alternatively, these agents may be part of a single dosage form, mixed together with the inhibitor in a single composition.

The pharmaceutical compositions of this invention may be administered orally, parenterally, by inhalation spray, topically, rectally, nasally, buccally, vaginally or via an implanted reservoir. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical, compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

According to another embodiment, compounds of formula (I) may also be delivered by implantation (e.g., surgically), such as with an implantable or indwelling device. An implantable or indwelling device may be designed to reside either permanently or temporarily in a subject. Examples of implantable and indwelling devices include, but are not limited to, contact lenses, central venous catheters and needleless connectors, endotracheal tubes, intrauterine devices, mechanical heart valves, pacemakers, peritoneal dialysis catheters, prosthetic joints, such as hip and knee replacements, tympanostomy tubes, urinary catheters, voice prostheses, stents, delivery pumps, vascular filters and implantable control release compositions. Biofilms can be detrimental to the health of patients with an implantable or indwelling medical device because they introduce an artificial substratum into the body and can cause persistent infections. Thus, providing compounds of formula (I) in or on the implantable or indwelling device can prevent or reduce the production of a biofilm. In addition, implantable or indwelling devices may be used as a depot or reservoir of compounds of formula (I). Any implantable or indwelling device can be used to deliver compounds of formula (I) provided that a) the device, compounds of formula (I) and any pharmaceutical composition including compounds of formula (I) are biocompatible, and b) that the device can deliver or release an effective amount of compounds of formula (I) to confer a therapeutic effect on the treated patient.

Delivery of therapeutic agents via implantable or indwelling devices is known in the art. See for example, "Recent Developments in Coated Stents" by Hofma et al. published in *Current Interventional Cardiology Reports* 2001, 3:28-36, the entire contents of which, including references cited therein, incorporated herein by reference. Other descriptions of implantable devices can be found in U.S. Pat. Nos. 6,569, 195 and 6,322,847; and U.S. Patent Application Numbers 2004/0044405, 2004/0018228, 2003/0229390, 2003/0225450, 2003/0216699 and 2003/0204168, each of which is incorporated herein by reference in its entirety.

In some embodiments, the implantable device is a stent. In one specific embodiment, a stent can include interlocked meshed cables. Each cable can include metal wires for structural support and polymeric wires for delivering the therapeutic agent. The polymeric wire can be dosed by immersing the polymer in a solution of the therapeutic agent. Alternatively, the therapeutic agent can be embedded in the polymeric wire during the formation of the wire from polymeric precursor solutions.

In other embodiments, implantable or indwelling devices can be coated with polymeric coatings that include the therapeutic agent. The polymeric coating can be designed to control the release rate of the therapeutic agent. Controlled release of therapeutic agents can utilize various technologies. Devices are known that have a monolithic layer or coating incorporating a heterogeneous solution and/or dispersion of an active agent in a polymeric substance, where the diffusion of the agent is rate limiting, as the agent diffuses through the polymer to the polymer-fluid interface and is released into the surrounding fluid. In some devices, a soluble substance is also dissolved or dispersed in the polymeric material, such that additional pores or channels are left after the material dissolves. A matrix device is generally diffusion limited as well, but with the channels or other internal geometry of the device also playing a role in releasing the agent to the fluid. The channels can be pre-existing channels or channels left behind by released agent or other soluble substances.

Erodible or degradable devices typically have the active agent physically immobilized in the polymer. The active agent can be dissolved and/or dispersed throughout the polymeric material. The polymeric material is often hydrolytically degraded over time through hydrolysis of labile bonds, allowing the polymer to erode into the fluid, releasing the active agent into the fluid. Hydrophilic polymers have a generally faster rate of erosion relative to hydrophobic polymers. Hydrophobic polymers are believed to have almost purely surface diffusion of active agent, having erosion from the surface inwards. Hydrophilic polymers are believed to allow water to penetrate the surface of the polymer, allowing hydrolysis of labile bonds beneath the surface, which can lead to homogeneous or bulk erosion of polymer.

The implantable or indwelling device coating can include a blend of polymers each having a different release rate of the therapeutic agent. For instance, the coating can include a polylactic acid/polyethylene oxide (PLA-PEO) copolymer and a polylactic acid/polycaprolactone (PLA-PCL) copolymer. The polylactic acid/polyethylene oxide (PLA-PEO) copolymer can exhibit a higher release rate of therapeutic agent relative to the polylactic acid/polycaprolactone (PLA-PCL) copolymer. The relative amounts and dosage rates of therapeutic agent delivered over time can be controlled by controlling the relative amounts of the faster releasing polymers relative to the slower releasing polymers. For higher initial release rates the proportion of faster releasing polymer can be increased relative to the slower releasing polymer. If most of the dosage is desired to be released over a long time period, most of the polymer can be the slower releasing polymer. The device can be coated by spraying the device with a solution or dispersion of polymer, active agent, and solvent. The solvent can be evaporated, leaving a coating of polymer and active agent. The active agent can be dissolved and/or dispersed in the polymer. In some embodiments, the co-polymers can be extruded over the device.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections.

Typically, the pharmaceutical compositions of this invention will be administered from about 1 to 5 times per day or alternatively, as a continuous infusion. Alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula (I) and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

According to another embodiment, the invention provides methods for treating or preventing a bacterial infection, or disease state, comprising the step of administering to a patient any compound, pharmaceutical composition, or combination described herein. The term "patient", as used herein, means an animal, preferably a mammal, and most preferably a human.

The compounds of this invention are also useful as commercial reagents which effectively bind to the gyrase B and/or topoisomerase IV enzymes. As commercial reagents, the compounds of this invention, and their derivatives, may be used to block gyrase B and/or topoisomerase IV activity in biochemical or cellular assays for bacterial gyrase B and/or topoisomerase IV or their homologs or may be derivatized to bind to a stable resin as a tethered substrate for affinity chromatography applications. These and other uses which characterize commercial gyrase B and/or topoisomerase IV inhibitors will be evident to those of ordinary skill in the art.

The compounds of this invention may be prepared by first synthesizing (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea (Compound 23 below) in accordance with general methods known to those skilled in the art for analogous compounds, as taught by U.S. Pat. No. RE40245 E; U.S. Pat. No. 7,495,014 B2; U.S. Pat. No. 7,569,591 B2; U.S. Pat. No. 7,582,641 B2; U.S. Pat. No. 7,618,974 B2; and U.S. Pat. No. 7,727,992 B2. All six of said patents are incorporated by reference as if fully set forth herein. The details of the conditions used for preparing the compounds of the present invention are further set forth in the Examples. The (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea 23 may then be converted to the phosphate or phosphate salt prodrugs according to Scheme 1 below.

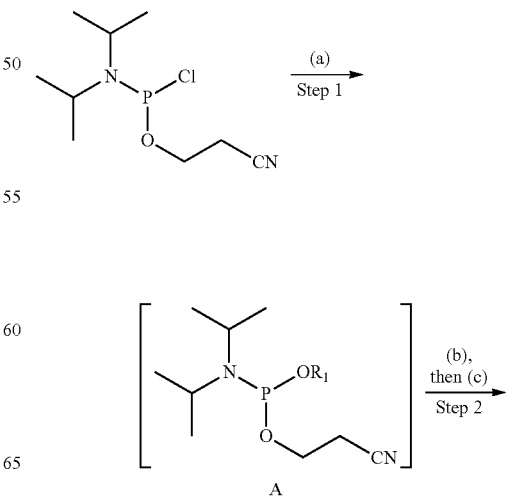

-continued

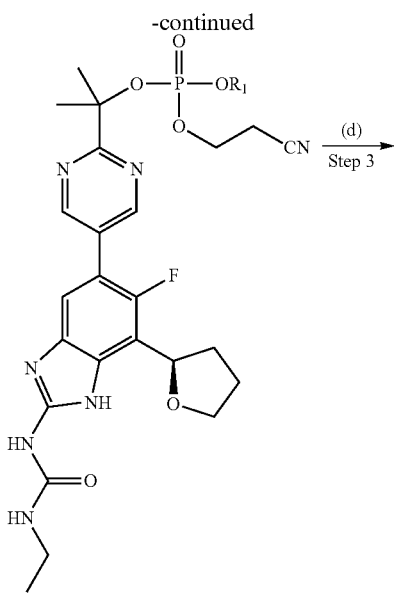

B

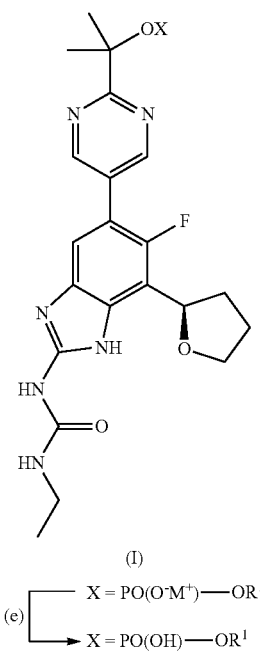

(I)

(e) ⌈ X = PO(O⁻M⁺)—OR¹
    ⌊→ X = PO(OH)—OR¹

Reagents and conditions: (a) R¹OH, DIPEA, 23° C., DCM; (b) 23, tetrazole, MeCN, DMF, 23° C.; (c) mCPBA, 0-23° C., DMF; (d) aq M⁺OH⁻; (e) aq H.

Compounds of formula (I) may be prepared from compound 23 as shown in Scheme 1. In Step 1,3-((chloro(diisopropylamino)phosphino)oxy)propanenitrile is treated with an alcohol (R¹OH) in the presence of diisopropylethylamine (DIPEA) to afford a reactive phosphoramidite A in situ. In Step 2, compound 23 is treated with the phosphoramidite A and tetrazole, followed by meta-chloroperoxybenzoic acid (mCPBA), to afford a cyanoethylphosphate B. In Step 3, the cyanoethylphosphate B is treated with aqueous M⁺OH⁻ to afford the anionic form of the compound of formula (I) (X=PO(O⁻M⁺)—OR¹). The free acid form of the compound of formula (I) (X=PO(OH)—OR¹) may be obtained by treating the anionic form with aqueous acid.

In order that this invention be more fully understood, the following examples are set forth. These examples are for the purpose of illustration only and are not to be construed as limiting the scope of the invention in any way.

The following definitions describe terms and abbreviations used herein:
Ac acetyl
Bu butyl
Et ethyl
Ph phenyl
Me methyl
THF tetrahydrofuran
DCM dichloromethane
$CH_2Cl_2$ dichloromethane
EtOAc ethyl acetate
$CH_3CN$ acetonitrile
EtOH ethanol
$Et_2O$ diethyl ether
MeOH methanol
MTBE methyl tert-butyl ether
DMF N,N-dimethylformamide
DMA N,N-dimethylacetamide
DMSO dimethyl sulfoxide
HOAc acetic acid
TEA triethylamine
TFA trifluoroacetic acid
TFAA trifluoroacetic anhydride
$Et_3N$ triethylamine
DIPEA diisopropylethylamine
DIEA diisopropylethylamine
$K_2CO_3$ potassium carbonate
$Na_2CO_3$ sodium carbonate
$Na_2S_2O_3$ sodium thiosulfate
$Cs_2CO_3$ cesium carbonate
$NaHCO_3$ sodium bicarbonate
NaOH sodium hydroxide
$Na_2SO_4$ sodium sulfate
$MgSO_4$, magnesium sulfate
$K_3PO_4$ potassium phosphate
$NH_4Cl$ ammonium chloride
LC/MS liquid chromatography/mass spectra
GCMS gas chromatography mass spectra
HPLC high performance liquid chromatography
GC gas chromatography
LC liquid chromatography
IC ion chromatography
IM intramuscular
CFU/cfu colony forming units
MIC minimum inhibitory concentration
hr or h hours
atm atmospheres
rt or RT room temperature
TLC thin layer chromatography
HCl hydrochloric acid
$H_2O$ water
EtNCO ethyl isocyanate
Pd/C palladium on carbon
NaOAc sodium acetate
$H_2SO_4$ sulfuric acid
$N_2$ nitrogen gas
$H_2$ hydrogen gas
n-BuLi n-butyl lithium
DI de-ionized
$Pd(OAc)_2$ palladium(II)acetate
$PPh_3$ triphenylphosphine
i-PrOH isopropyl alcohol
NBS N-bromosuccinimide
$Pd[(Ph_3)P]_4$ tetrakis(triphenylphosphine)palladium(0)
PTFE polytetrafluoroethylene rpm revolutions per minute
SM starting material
Equiv. equivalents
$^1$H-NMR proton nuclear magnetic resonance
mCPBA meta-chloroperoxybenzoic acid
aq aqueous
Boc$_2$O di-tert-butyl dicarbonate
DMAP N,N-dimethylaminopyridine
mL milliliters
mol moles
g grams
LCMS liquid chromatography-mass spectrometry
MHz megahertz
CDCl$_3$ deuteriochloroform
NEt$_3$ triethylamine
mmol millimoles
psi pounds per square inch
iPrOH isopropylalcohol
ppm parts per million
NH$_4$NO$_3$ ammonium nitrate
Hz hertz
Pd(dppf)Cl$_2$ [1,1'-Bis(diphenylphosphino)ferrocene]dichloropalladium(II)
L liters
MeOD deutero-methanol
CD$_3$OD deuteron-methanol
ee enantiomeric excess
min minutes
MeCN acetonitrile
mg milligrams
μL microliters
MPLC medium pressure liquid chromatography
ESMS electrospray mass spectrometry
OBD optimal bed density
NH$_4$OH ammonium hydroxide
M molar
ATP adenosine triphosphate
ADP adenosine diphosphate
NADH nicotinamide adenine dinucleotide (reduced form)
NAD+ nicotinamide adenine dinucleotide (oxidized form)
TRIS tris(hydroxymethyl)aminomethane
mM millimolar
MgCl$_2$ magnesium chloride
KCl potassium chloride
μM micromolar
DTT dithiothreitol
nM nanomolar
K$_i$ dissociation constant
μg micrograms
BSA bovine serum albumin
LDH lactate dehydrogenase
PVDF polyvinylidene fluoride
AcN acetonitrile
General Experimental Procedures
Elemental Analysis.
Elemental analysis was conducted separately for carbon, hydrogen, and nitrogen (CHN); fluorine (F); and phosphorus (P). CHN percentages were determined by combustion analysis using a Perkin-Elmer 2400 Elemental Analyzer. F percentages were determined by the ion specific electrode technique. P percentages were determined by were determined by inductively coupled plasma spectrometry using a Perkin-Elmer Optima ICP spectrometer.
Part I: Synthesis of Intermediate Compound 23
A synthetic method to prepare compound 23 from commercially available material is provided in the experimental procedures below. Compound 23 is an intermediate used in the synthesis of the phosphate esters of formula (I).

Preparation 1

Preparation of 2-(2-fluoro-6-nitro-phenyl)-2,3-dihydrofuran (15A) and 2-(2-fluoro-6-nitro-phenyl)-2,5-dihydrofuran (15B)

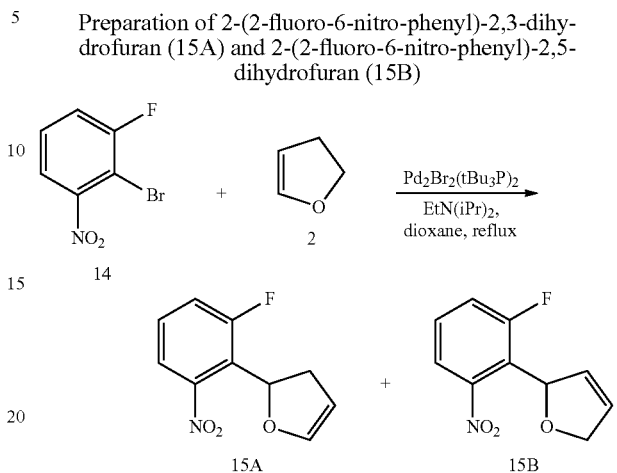

2-Bromo-1-fluoro-3-nitro-benzene (14) (200.3 g, 98%, 892.3 mmol, Bosche F6657), 1,4-dioxane (981.5 mL, Sigma-Aldrich 360481), and 2,3-dihydrofuran (2) (341.1 mL, 99%, 4.462 mol, Aldrich 200018) were charged in a reaction flask, followed by N,N-diisopropylethylamine (155.4 mL, 892.3 mmol, Sigma-Aldrich 550043) and bromo(tri-tert-butylphosphine)palladium(I) dimer (6.936 g, 8.923 mmol, Johnson Matthey C4099). The mixture was stirred at reflux for 2 hrs (HPLC showed 98% consumption of starting arylbromide). It was allowed to cool, the precipitate was removed by filtration, rinsed with EtOAc, and the filtrate concentrated in vacuo to a dark reddish brown semi-solid oil. This was dissolved in CH$_2$Cl$_2$, eluted through a plug of silica with CH$_2$Cl$_2$, and concentrated in vacuo giving a mixture of 15A and 15B as a dark amber oil (291.3 g). The crude product was carried forward without further purification. The major product was 2-(2-fluoro-6-nitro-phenyl)-2,3-dihydrofuran (15A) (96%): LCMS (C18 column eluting with 10-90% CH$_3$CN/water gradient over 5 minutes with formic acid modifier) M+1: 210.23 (3.13 min); $^1$H NMR (300 MHz, CDCl$_3$) δ 7.54 (dt, J=8.0, 1.2 Hz, 1H), 7.43 (td, J=8.2, 5.2 Hz, 1H), 7.32 (ddd, J=9.7, 8.3, 1.3 Hz, 1H), 6.33 (dd, J=4.9, 2.4 Hz, 1H), 5.80 (t, J=10.9 Hz, 1H), 5.06 (q, J=2.4 Hz, 1H), 3.18-3.07 (m, 1H), 2.94-2.82 (m, 1H) ppm. The minor product was 2-(2-fluoro-6-nitro-phenyl)-2,5-dihydrofuran (15B) (4%): GCMS (Agilent HP-5MS 30 m×250 μm×0.25 μm column heating at 60° C. for 2 min to 300° C. over 15 min with a 1 mL/min flow rate) M+1: 210 (11.95 min). $^1$H NMR (300 MHz, CDCl$_3$) δ 7.47 (d, J=8.0 Hz, 1H), 7.43-7.34 (m, 1H), 7.30-7.23 (m, 1H), 6.21-6.15 (m, 1H), 6.11-6.06 (m, 1H), 5.97-5.91 (m, 1H), 4.89-4.73 (m, 2H) ppm.

Preparation 2

Preparation of 3-fluoro-2-tetrahydrofuran-2-yl-aniline (16)

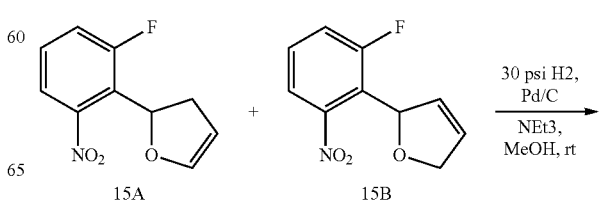

-continued

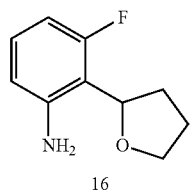

16

Placed 5% palladium on carbon (37.3 g, 50% wet, 8.76 mmol, Aldrich 330116) in a Parr bottle under nitrogen, followed by MeOH (70 mL, JT-Baker 909333). Added the crude mixture of 2-(2-fluoro-6-nitro-phenyl)-2,3-dihydrofuran and 2-(2-fluoro-6-nitro-phenyl)-2,5-dihydrofuran (15A&15B) (186.6 g, 892.1 mmol) dissolved in MeOH (117 mL), followed by NEt₃ (124.3 mL, 892.1 mmol, Sigma-Aldrich 471283). Placed the vessel on a Parr shaker and saturated with H₂. After adding 45 psi H₂, the reaction mixture was shaken until consumption of the starting material was complete (HPLC and LCMS showed complete reaction). The reaction mixture was purged with nitrogen, filtered through Celite™ and rinsed with EtOAc. The filtrate was concentrated on a rotary evaporator giving a brown oil, which was dissolved in Et₂O and washed with water (2×). The ether phase was extracted with aqueous 1N HCl (5×250 mL), which was washed with Et₂O (3×) and then basified with aqueous 6 N NaOH to pH 12-14. The basic aqueous phase was extracted with CH₂Cl₂ (4×), and the combined organic extract washed with saturated aqueous NH₄Cl, dried over MgSO₄, and filtered through a pad of silica eluting with CH₂Cl₂ to 25% EtOAc/hexane. The desired filtrate was concentrated under reduced pressure giving 16 as a light brown oil (121.8 g, 84% GCMS plus NMR purity). GCMS (Agilent HP-5MS 30 m×250 µm×0.25 µm column heating at 60° C. for 2 min to 300° C. over 15 min with a 1 mL/min flow rate) M+1: 182.0 (11.44 min). LCMS (C18 column eluting with 10-90% CH₃CN/water gradient over 5 minutes with formic acid modifier) M+1: 182.10 (2.61 min). ¹H NMR (300 MHz, CDCl₃) δ 6.97 (td, J=8.1, 6.3 Hz, 1H), 6.43-6.35 (m, 2H), 5.21-5.13 (m, 1H), 4.54 (s, 2H), 4.16-4.07 (m, 1H), 3.90-3.81 (m, 1H), 2.23-2.00 (m, 4H) ppm. Additional crops were obtained as follows: the combined ether phase was washed with saturated aqueous NaHCO₃, brine, dried over Na₂SO₄, decanted, and concentrated under reduced pressure. The oil was vacuum distilled (ca. 15 torr) collecting the distillate at 101-108° C. To a stirring solution of the distilled oil in EtOH (1 volume) at 2° C. was slowly added 5 M HCl (1 eq) in iPrOH. The resulting suspension was brought to room temperature, diluted with EtOAc (3 volumes, vol/vol), and stirred for 2 hrs. The white solid was collected by filtration, washed with EtOAc, and dried under reduced pressure giving a second crop of product as the HCl salt. The mother liquor was concentrated to a slurry, diluted with EtOAc and the solid collected by filtration, washed with EtOAc, and dried in vacuo giving the HCl salt as a third crop of the product. LCMS (C18 column eluting with 10-90% CH₃CN/water gradient over 5 minutes with formic acid modifier) M+1: 182.10 (2.58 min). ¹H NMR (300 MHz, CDCl₃) δ 10.73 (br.s, 3H), 7.66 (d, J=8.1 Hz, 1H), 7.33 (td, J=8.2, 5.9 Hz, 1H), 7.13-7.05 (m, 1H), 5.26 (dd, J=9.0, 6.5 Hz, 1H), 4.38-4.28 (m, 1H), 4.00-3.91 (m, 1H), 2.59-2.46 (m, 1H), 2.30-1.95 (m, 3H) ppm. The overall yield from the three crops was 76%.

Preparation 3

Preparation of 4-bromo-3-fluoro-2-tetrahydrofuran-2-yl-aniline (17)

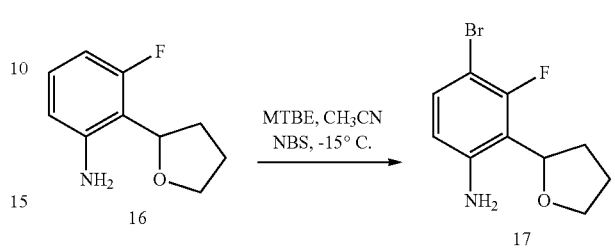

To a stirring solution of 3-fluoro-2-tetrahydrofuran-2-yl-aniline (16) (131.9 g, 92%, 669.7 mmol) in methyl tert-butyl ether (1.456 L) and acetonitrile (485 mL) cooled to −20° C. was added N-bromosuccinimide (120.4 g, 99%, 669.7 mmol, Aldrich B81255) in 3 portions maintaining a reaction temperature below about −15° C. After complete addition stirring was continued at −15 to −10° C. for 30 minutes. ¹H NMR of a worked-up aliquot showed 96% consumption of starting aniline so added another 4.82 g NBS and stirred at −10° C. for another 30 minutes. Aqueous 1N Na₂S₂O₃ (670 mL) was added to the reaction mixture. The cold bath was removed, the mixture stirred for 20 minutes, then diluted with EtOAc. The layers were separated and the organic phase was washed with saturated aqueous NaHCO₃ (2×), water, brine, dried over Na₂SO₄, decanted, and concentrated under reduced pressure giving a dark amber oil. The residue was diluted with hexane and eluted through a short plug of silica eluting with 25% EtOAc/hexane to 50% EtOAc/hexane. The desired filtrate was concentrated in vacuo giving 17 as a dark amber oil (182.9 g, 90% yield; 86% NMR purity). LCMS (C18 column eluting with 10-90% CH₃CN/water gradient over 5 minutes with formic acid modifier) M+1: 260.12 (3.20 min). ¹H NMR (300 MHz, CDCl₃) δ 7.15 (dd, J=8.6, 7.6 Hz, 1H), 6.30 (dd, J=8.7, 1.3 Hz, 1H), 5.19-5.12 (m, 1H), 4.58 (s, 2H), 4.16-4.07 (m, 1H), 3.90-3.81 (m, 1H), 2.23-1.99 (m, 4H) ppm.

Preparation 4

Preparation of N-(4-bromo-3-fluoro-6-nitro-2-tetrahydrofuran-2-yl-phenyl)-2,2,2-trifluoro-acetamide (18)

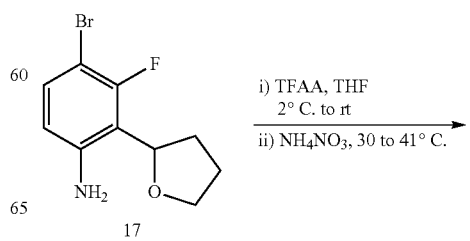

-continued

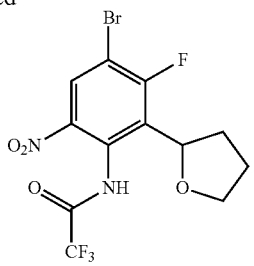

18

To trifluoroacetic anhydride (565.3 mL, 4.067 mol, Sigma-Aldrich 106232) stirring at 2° C. was slowly added neat 4-bromo-3-fluoro-2-tetrahydrofuran-2-yl-aniline (17) (123.0 g, 86%, 406.7 mmol) as a thick oil via addition funnel over about 20 minutes (reaction temperature rose to 13° C.). The remaining oil was rinsed into the reaction mixture with anhydrous THF (35 mL). The cold bath was removed and the reaction was heated to 35° C., followed by portion-wise addition of NH₄NO₃ (4.88 g×20 portions, 1.22 mol, Sigma-Aldrich A7455) over 2.5 hrs maintaining the reaction temperature between 30 and 41° C. using an ice-water bath only as needed to control the exotherm. After complete addition the reaction mixture was stirred for another 10 minutes (HPLC showed reaction 99% complete). It was slowly poured into crushed ice (1.23 kg) and stirred for 1 hr to allow formation of a filterable solid precipitate, which was collected and washed with water, sparingly with saturated aqueous NaHCO₃, and water again (to pH 7). The product was dried in a convection oven overnight at 40° C. and then under reduced pressure in an oven at 50° C. overnight giving 18 as a beige solid (152.5 g, 90% yield; 96% HPLC purity). LCMS (C18 column eluting with 10-90% CH₃CN/water gradient over 5 minutes with formic acid modifier) M+1: 401.30 (3.41 min). ¹H NMR (300 MHz, CDCl₃) δ 10.56 (s, 1H), 8.19 (d, J=6.6 Hz, 1H), 5.22 (dd, J=10.3, 6.4 Hz, 1H), 4.22 (dd, J=15.8, 7.2 Hz, 1H), 3.99 (dd, J=16.1, 7.5 Hz, 1H), 2.50-2.38 (m, 1H), 2.22-2.11 (m, 2H), 1.86-1.71 (m, 1H) ppm.

Preparation 5

Preparation of 4-bromo-3-fluoro-6-nitro-2-tetrahydrofuran-2-yl-aniline (19)

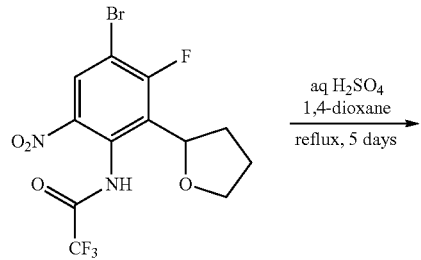

-continued

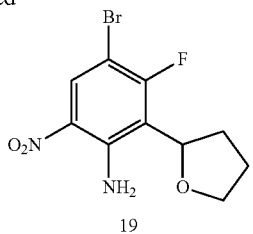

19

A reaction flask was charged with N-(4-bromo-3-fluoro-6-nitro-2-tetrahydrofuran-2-yl-phenyl)-2,2,2-trifluoro-acetamide (18) (242.3 g, 604.1 mmol), 1,4-dioxane (1.212 L), aqueous 2 M sulfuric acid (362.4 mL, 724.9 mmol), and stirred at reflux for 5 days (HPLC showed 98% conversion). Allowed to cool, diluted with EtOAc, neutralized with saturated aqueous NaHCO₃, separated the layers, and re-extracted the aqueous phase with EtOAc (2×). The combined organic phase was washed with brine (2×), dried over MgSO₄, filtered and concentrated in vacuo giving 19 as a greenish brown solid (181.7 g, 94% yield; 95% HPLC purity). The product was carried to the next step without further purification. LCMS (C18 column eluting with 10-90% CH₃CN/water gradient over 5 minutes with formic acid modifier) M+1: 305.20 (3.63 min). ¹H NMR (300 MHz, CDCl₃) δ 8.35 (d, J=7.3 Hz, 1H), 7.45 (s, 2H), 5.23-5.16 (m, 1H), 4.23-4.14 (m, 1H), 3.93-3.84 (m, 1H), 2.31-1.96 (m, 4H) ppm.

Preparation 6

Preparation of 2-[5-(4-amino-2-fluoro-5-nitro-3-tetrahydrofuran-2-yl-phenyl)pyrimidin-2-yl]propan-2-ol (20)

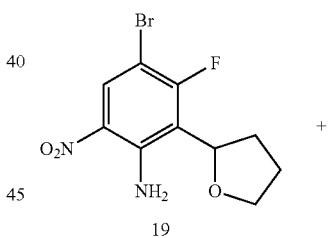

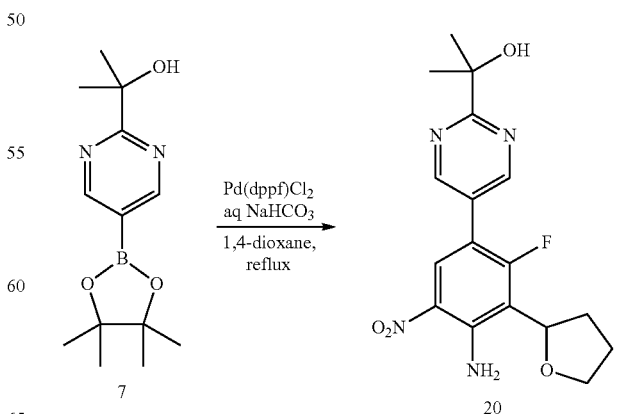

To a stirring solution of 4-bromo-3-fluoro-6-nitro-2-tetrahydrofuran-2-yl-aniline (19) (525.0 g, 1.721 mol, Bridge Organics Co.) in 1,4-dioxane (4.20 L, Sigma-Aldrich 360481) was added a 1.2 M aqueous solution of NaHCO$_3$ (4.302 L, 5.163 mol). A stream of nitrogen was bubbled through the stirring mixture for 2 hrs, followed by addition of 2-[5-(4,4,5,5-tetramethyl-1,3,2-dioxaborolan-2-yl)pyrimidin-2-yl]propan-2-ol (7) (545.4 g, 2.065 mol, Bridge Organics Co.) and 1,1'-bis(diphenylphosphino)ferrocene dichloropalladium dichloromethane adduct (42.16 g, 51.63 mmol, Strem 460450). The reaction mixture was stirred at reflux overnight, allowed to cool, diluted with EtOAc (8.4 L), and the layers were separated. The organic phase was washed with saturated aqueous NH$_4$Cl and then brine. The aqueous phase was re-extracted with EtOAc (4 L) and washed this organic extract with brine. The combined organic phase was dried over MgSO$_4$, filtered through a short plug of Florisil®, eluted with EtOAc, and the filtrate concentrated on a rotary evaporator giving a dark brown wet solid. This was dissolved in CH$_2$Cl$_2$, loaded on a pad of silica gel, eluted with hexane, then 25% EtOAc/hexane, and then 50% EtOAc/hexane. The desired filtrate was concentrated on a rotary evaporator to a thick suspension, and the solid was collected by filtration, triturated with MTBE, and dried in vacuo giving 20 as a bright yellow solid (55.8% yield, 90-97% HPLC purity). The filtrate was concentrated and the above purification was repeated giving a second crop of 20 as a bright yellow solid (19.7% yield). The filtrate was again concentrated giving a dark brown oil and this was loaded on a silica column with toluene and minimal CH$_2$Cl$_2$. It was eluted with EtOAc/hexane (0% to 50%). The desired fractions were concentrated to a slurry and diluted with MTBE/hexane. The solid was collected by filtration and washed with minimal MTBE giving a third crop of 20 as a bright yellow solid (4.9% yield) with an overall yield of 80% from the three crops. LCMS (C18 column eluting with 10-90% CH$_3$CN/water gradient over 5 minutes with formic acid modifier) M+1: 363.48 (2.95 min). $^1$H NMR (300 MHz, CDCl$_3$) δ 8.84 (d, J=1.6 Hz, 2H), 8.27 (d, J=8.0 Hz, 1H), 7.62 (s, 2H), 5.31-5.24 (m, 1H), 4.63 (s, 1H), 4.27-4.18 (m, 1H), 3.97-3.87 (m, 1H), 2.33-2.05 (m, 4H), 1.64 (s, 6H) ppm.

Preparation 7

Preparation of 2-[5-(4,5-diamino-2-fluoro-3-tetrahydrofuran-2-yl-phenyl)pyrimidin-2-yl]propan-2-ol (21)

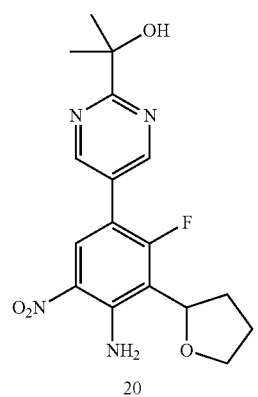

20

45 psi H$_2$, Pd/C, NEt$_3$
MeOH, THF
→

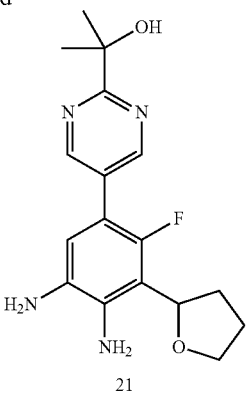

21

Placed 5% palladium on carbon (14.21 g, 50% wet, 3.339 mmol, Aldrich 330116) in a Parr bottle under nitrogen, followed by MeOH (242 mL, JT-Baker 909333) and NEt$_3$ (46.54 mL, 333.9 mmol, Sigma-Aldrich 471283). Dissolved 2-[5-(4-amino-2-fluoro-5-nitro-3-tetrahydrofuran-2-yl-phenyl)pyrimidin-2-yl]propan-2-ol (20) (121.0 g, 333.9 mmol) in hot THF (360 mL), allowed to cool, added to the reaction mixture, and rinsed with another portion of THF (124 mL). Placed the vessel on a Parr shaker and saturated with H$_2$. Added 45 psi H$_2$ and shook until consumption complete (HPLC and LCMS showed complete reaction). The reaction mixture was purged with nitrogen, filtered through Celite™ and rinsed with EtOAc. It was re-filtered through paper (glass microfibre) and the filtrate concentrated in vacuo. Repeated the reaction three more times on the same scale and the batches were combined giving 21 as a brown solid (447 g, 99% yield; 93% HPLC purity). LCMS (C18 column eluting with 10-90% CH$_3$CN/water gradient over 5 minutes with formic acid modifier) M+1: 333.46 (1.79 min). $^1$H NMR (300 MHz, CDCl$_3$) δ 8.81 (d, J=1.4 Hz, 2H), 6.69 (d, J=7.3 Hz, 1H), 5.27-5.20 (m, 1H), 4.73 (s, 1H), 4.70 (s, 2H), 4.23-4.14 (m, 1H), 3.94-3.86 (m, 1H), 3.22 (s, 2H), 2.32-2.22 (m, 1H), 2.18-1.99 (m, 3H), 1.63 (s, 6H) ppm.

Preparation 8

Preparation of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22)

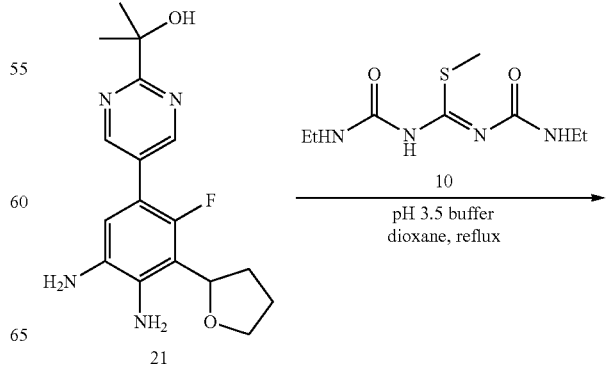

21

10
pH 3.5 buffer
dioxane, reflux
→

Preparation 9

Chiral chromatographic isolation of (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea (23)

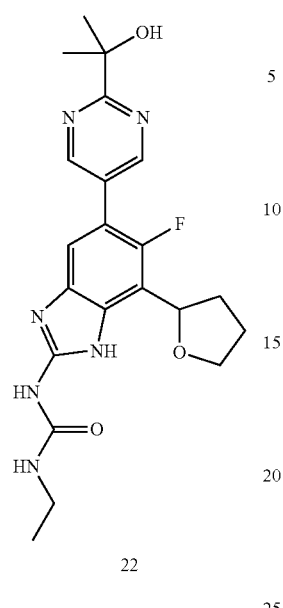

22

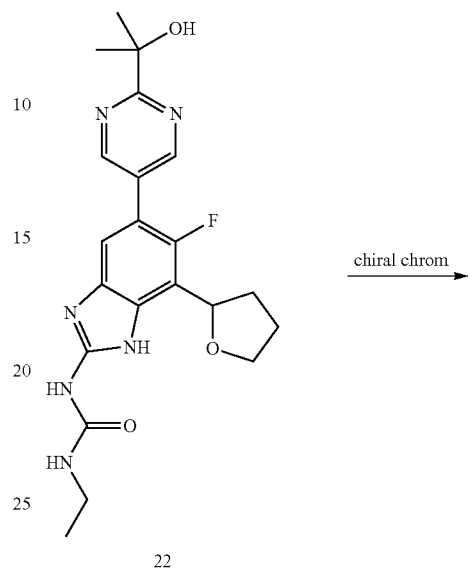

22

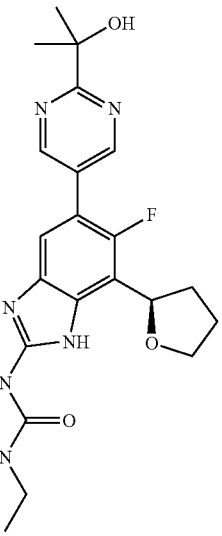

23

To a stirring suspension of 2-[5-(4,5-diamino-2-fluoro-3-tetrahydrofuran-2-yl-phenyl)pyrimidin-2-yl]propan-2-ol (21) (111.3 g, 334.9 mmol) and 1,4-dioxane (556.5 mL, Sigma-Aldrich 360481) was added 1-ethyl-3-(N-(ethylcarbamoyl)-C-methylsulfanyl-carbonimidoyl)urea (10) (93.36 g, 401.9 mmol, CB Research and Development) followed by a pH 3.5 buffer (1.113 L), prepared by dissolving NaOAc trihydrate (158.1 g) in 1N aqueous $H_2SO_4$ (1.100 L). The reaction mixture was stirred at reflux overnight (HPLC showed complete conversion), cooled to room temperature, and poured portion-wise (frothing) into a stirring solution of aqueous saturated $NaHCO_3$ (2.23 L) giving pH 8-9. This was stirred for 30 minutes, the solid was collected by filtration, washed copiously with water to neutral pH, and then more sparingly with EtOH. The solid was dried under reduced pressure giving 22 as an off-white yellowish solid (135.2 g, 94% yield; 99% HPLC purity). LCMS (C18 column eluting with 10-90% $CH_3CN$/water gradient over 5 minutes with formic acid modifier) M+1: 429.58 (2.03 min). $^1$H NMR (300 MHz, MeOD) δ 8.95 (d, J=1.6 Hz, 2H), 7.45 (d, J=6.5 Hz, 1H), 5.38 (br.s, 1H), 4.27 (dd, J=14.9, 7.1 Hz, 1H), 4.01 (dd, J=15.1, 7.0 Hz, 1H), 3.37-3.29 (m, 2H), 2.55 (br.s, 1H), 2.19-2.07 (m, 2H), 2.02-1.82 (br.s, 1H), 1.63 (s, 6H), 1.21 (t, J=7.2 Hz, 3H) ppm.

A racemic sample of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22) (133.60 g) was resolved on a CHIRALPAK® IC® column (by Chiral Technologies) eluting with DCM/MeOH/TEA (60/40/0.1) at 25° C. giving the desired enantiomer 23 as an off-white solid (66.8 g, 45% yield; 99.8% HPLC purity, 99+% ee). Analytical chiral HPLC retention time was 7.7 min (CHIRALPAK® IC® 4.6×250 mm column, 1 mL/min flow rate, 30° C.). The solid was suspended in 2:1 EtOH/Et$_2$O (5 volumes), stirred for 10 minutes, collected by filtration, washed with 2:1 EtOH/Et$_2$O, and dried under reduced pressure giving a white solid (60.6 g).

The structure and absolute stereochemistry of 23 were confirmed by single-crystal x-ray diffraction analysis. Single crystal diffraction data were acquired on a Bruker Apex II diffractometer equipped with sealed tube Cu K-alpha source (Cu Kα radiation, γ=1.54178 Å) and an Apex II CCD detector. A crystal with dimensions of 0.15×0.15×0.10 mm was selected, cleaned using mineral oil, mounted on a Micro-Mount and centered on a Bruker APEXII system. Three batches of 40 frames separated in reciprocal space were obtained to provide an orientation matrix and initial cell parameters. Final cell parameters were obtained and refined after data collection was completed based on the full data set. Based on systematic absences and intensities statistics the structure was solved and refined in acentric P2$_1$ space group.

A diffraction data set of reciprocal space was obtained to a resolution of 0.85 Å using 0.5° steps using 30 s exposure for each frame. Data were collected at 100 (2) K. Integration of intensities and refinement of cell parameters were accomplished using APEXII software. Observation of the crystal after data collection showed no signs of decomposition. As shown in FIG. 1, there are two symmetry independent molecules in the structure and both symmetry independent molecules are R isomers.

The data were collected, refined and reduced using the Apex II software. The structure was solved using the SHELXS97 (Sheldrick, 1990); program(s) and the structure refined using the SHELXL97 (Sheldrick, 1997) program. The crystal shows monoclinic cell with P2$_1$ space group. The lattice parameters are a=9.9016(2) Å, b=10.9184(2) Å, c=19.2975(4) Å, β=102.826(1)°. Volume=2034.19(7) Å$^3$.

Part II: Synthesis of Phosphate Ester X of Formula (I)

Prodrug compound X may be prepared from compound 23 as shown in Scheme 1 according to the following experimental procedures.

X

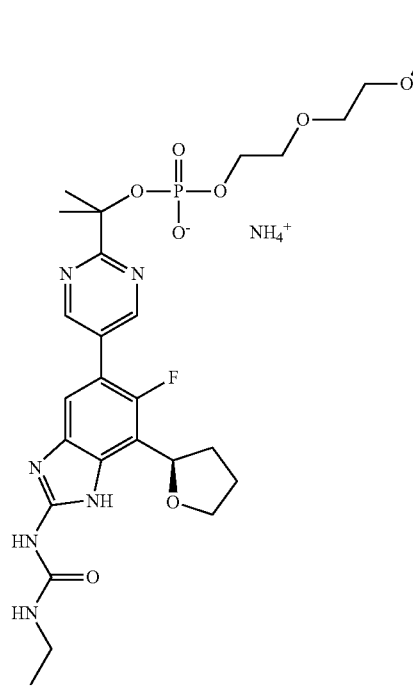

Preparation 16

Preparation of 2-cyanoethyl 2-(5-(2-(3-ethylureido)-6-fluoro-7-((R)-tetrahydrofuran-2-yl)-1H-benzo[d]imidazol-5-yl)pyrimidin-2-yl)propan-2-yl 2-(2-methoxyethoxy)ethyl phosphate (30)

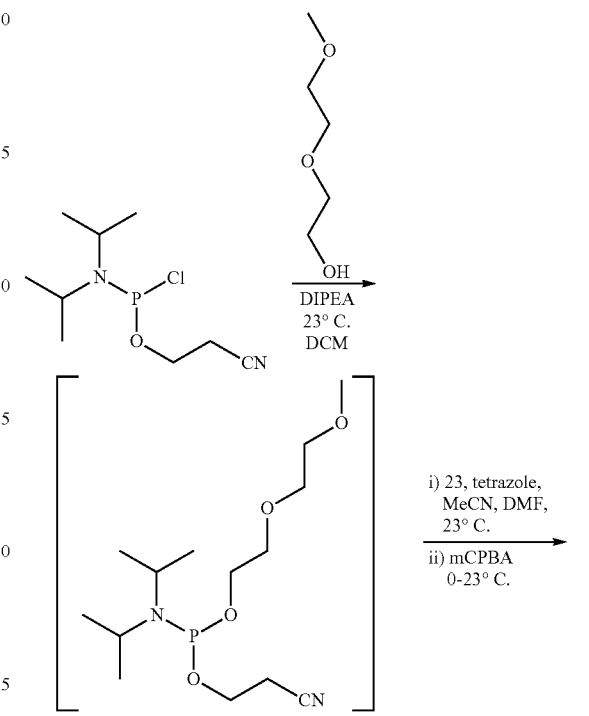

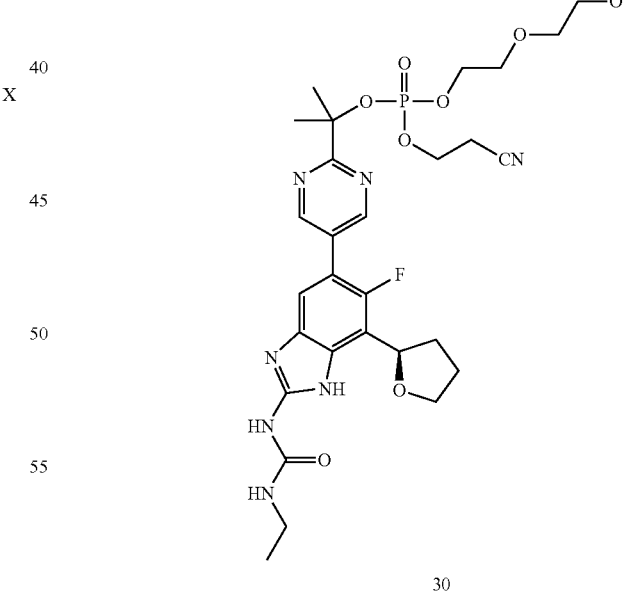

30

To a solution of DIPEA (366.3 mg, 493.7 µL, 2.834 mmol) in DCM (6 mL) at 23° C. under N$_2$ was added 3-[chloro-(diisopropylamino)phosphanyl]oxypropanenitrile (503.2 mg, 474.3 µL, 2.126 mmol) followed by 2-(2-methoxyethoxy)ethanol (255.4 mg, 252.9 µL, 2.126 mmol). In a separate flask under N$_2$ a suspension of (R)-1-ethyl-3-(6-fluoro- 5-(2-(2-hydroxypropan-2-yl)pyrimidin-5-yl)-7-(tetrahydrofuran-2-yl)-1H-benzo[d]imidazol-2-yl)urea(23) (607 mg, 1.417 mmol) in DMF (6 mL) was treated with tetrazole (0.45 M solution in MeCN, 6.298 mL, 2.834 mmol). After aging for 10 min the solution of phosphoramidite was added via syringe to the suspension of (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea (23) and tetrazole. The resulting reaction mixture was stirred for 3 h after which time it was cooled to 0° C. then treated with mCPBA (558.9 mg, 2.267 mmol). The mixture was stirred for 5 min at 0° C. then for 10 min at 23° C. after which time the crude reaction mixture was diluted with EtOAc (100 mL) and washed successively with saturated aqueous sodium bicarbonate, 10% aqueous sodium bisulfite, saturated aqueous sodium bicarbonate and brine (100 mL each), then dried (magnesium sulfate) filtered and concentrated in vacuo. The residue was purified by MPLC using an ISCO COMBI-FLASH brand flash chromatography purification system (80 g silica column) 0-13% EtOH in DCM linear gradient over 20 column volumes at 60 mL/min to give 2-cyanoethyl 2-(5-(2-(3-ethylureido)-6-fluoro-7-((R)-tetrahydrofuran-2-yl)-1H-benzo[d]imidazol-5-yl)pyrimidin-2-yl)propan-2-yl 2-(2-methoxyethoxy)ethyl phosphate (30) (734 mg, 1.106 mmol, 78.05%) as a clear glassy oil. ESMS (M+1)=664.5; $^1$H NMR shows doubling of some peaks, due to diastereomers (stereogenic phosphate); $^1$H NMR (300.0 MHz, CDCl$_3$) δ 8.90 (dd, J=1.1, 4.9 Hz, 2H), 7.20-7.15 (m, 1H), 5.31 (s, 1H), 4.57-4.23 (m, 4H), 4.16 (br s, 1H), 3.92 (dd, J=6.9, 14.2 Hz, 1H), 3.79-3.74 (m, 2H), 3.71-3.66 (m, 2H), 3.58-3.53 (m, 2H), 3.39 (d, J=3.6 Hz, 3H), 3.33 (br s, 2H), 3.04-2.85 (m, 2H), 2.50-2.46 (m, 1H), 2.04-1.80 (m, 9H) and 1.20 (t, J=6.9 Hz, 3H) ppm.

Example 1

Preparation of ammonium (R)-2-(5-(2-(3-ethylureido)-6-fluoro-7-(tetrahydrofuran-2-yl)-1H-benzo[d]imidazol-5-yl)pyrimidin-2-yl)propan-2-yl 2-(2-methoxyethoxy)ethyl phosphate (X)

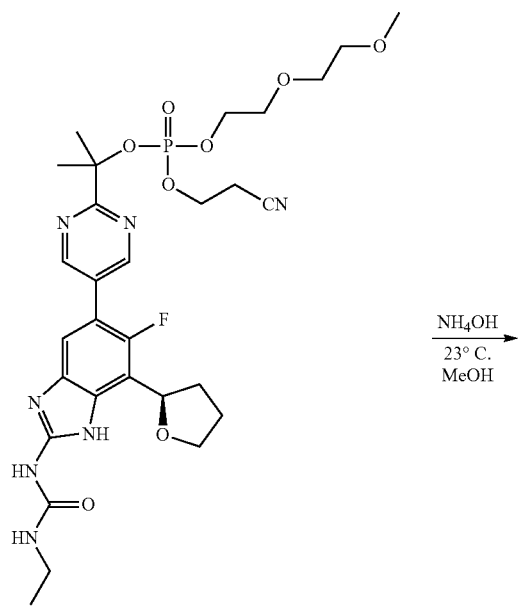

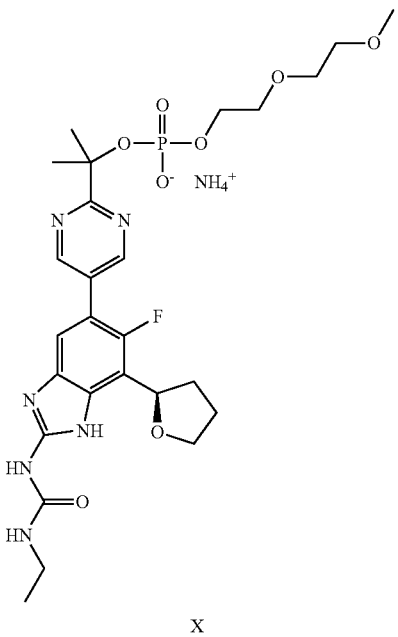

X

To a solution of 2-cyanoethyl 2-(5-(2-(3-ethylureido)-6-fluoro-7-((R)-tetrahydrofuran-2-yl)-1H-benzo[d]imidazol-5-yl)pyrimidin-2-yl)propan-2-yl 2-(2-methoxyethoxy)ethyl phosphate (30) (734 mg, 1.106 mmol) in MeOH (20 mL) at 23° C. was added ammonium hydroxide (430 μL, 11.04 mmol). After stirring for 16 hours, more ammonium hydroxide (1 mL) was added. After a further 4 hours, the reaction mixture was concentrated in vacuo. The residue was dissolved in MeOH (7 mL) and purified via preparative HPLC, 7 injections Using a Waters XBridge C18 5 μm OBD column (19×100 mm) eluting with a 10-90% aqueous MeCN with 0.1% NH$_4$OH buffer, gradient over 15 min at 20 mL/min flow rate. Product fractions were pooled, frozen and lyophilized to give ammonium (R)-2-(5-(2-(3-ethylureido)-6-fluoro-7-(tetrahydrofuran-2-yl)-1H-benzo[d]imidazol-5-yl)pyrimidin-2-yl)propan-2-yl 2-(2-methoxyethoxy)ethyl phosphate (X) (443 mg, 0.7010 mmol, 63.38%) as a white solid. ESMS (M+1)=611.5; $^1$H NMR (300.0 MHz, CD$_3$OD) δ 8.86 (d, J=1.0 Hz, 2H), 7.30 (d, J=6.3 Hz, 1H), 5.24 (t, J=7.6 Hz, 1H), 4.23 (dd, J=7.0, 14.8, 1H), 4.13-4.05 (m, 2H), 3.94 (dd, J=7.2, 15.0 Hz, 1H), 3.72-3.64 (m, 4H), 3.56-3.51 (m, 2H), 3.35 (s, 3H), 3.34-3.28 (m, 2H), 2.52-2.42 (m, 1H), 2.12-2.00 (m, 2H), 1.90 (d, J=1.6 Hz, 6H), 1.89-1.74 (m, 1H) and 1.22 (t, J=7.2 Hz, 3H) ppm. Elemental Analysis Calculated for C$_{26}$H$_{39}$FN$_7$O$_8$P (corrected for 4.73% w/w water, as determined by the Karl-Fischer oven method): C, 47.41; H, 6.49; N, 14.88; F, 2.89; P, 4.71. Found: C, 47.71; H, 6.27; N, 14.08; F, 2.93; P, 5.15.

Part III: Synthesis of Phosphate Ester Y of Formula (I)

Prodrug compound Y may be prepared from compound 23 as shown in Scheme 1 according to the following experimental procedures.

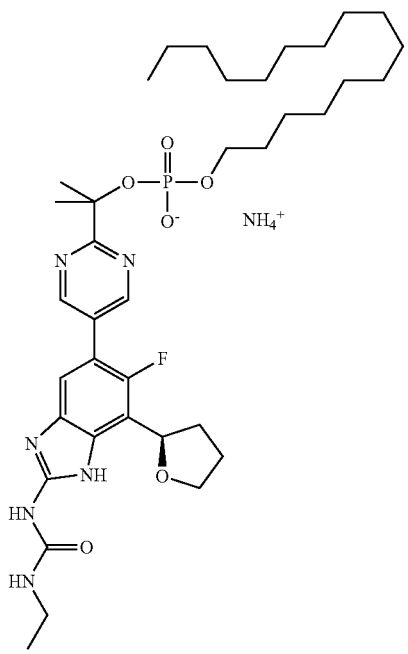

Preparation 17

Preparation of 2-cyanoethyl[1-[5-[2-(ethylcarbamoy-lamino)-6-fluoro-7-[(2R)-tetrahydrofuran-2-yl]-1H-benzimidazol-5-yl]pyrimidin-2-yl]-1-methyl-ethyl] hexadecyl phosphate (31)

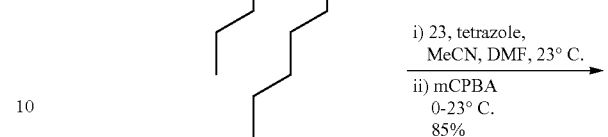

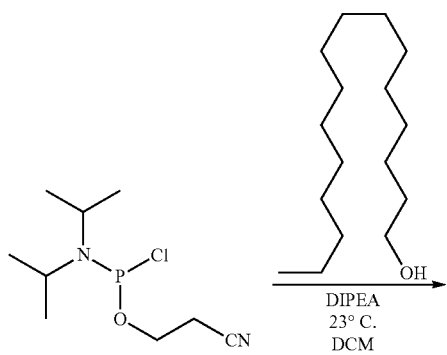

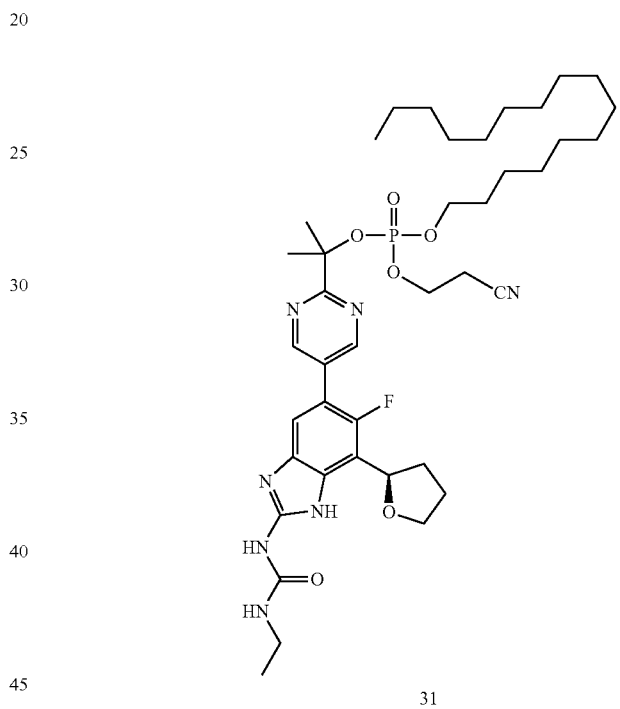

To a solution of hexadecan-1-ol (515.4 mg, 2.126 mmol) and DIPEA (366.3 mg, 493.7 μL, 2.834 mmol) in DCM (6 mL) at 23° C. under N₂ was added 3-[chloro-(diisopropy-lamino)phosphanyl]oxypropanenitrile (503.2 mg, 474.3 μL, 2.126 mmol). In a separate flask under N₂ a suspension of (R)-1-ethyl-3-(6-fluoro-5-(2-(2-hydroxypropan-2-yl)pyri-midin-5-yl)-7-(tetrahydrofuran-2-yl)-1H-benzo[d]imidazol-2-yl)urea (23) (607 mg, 1.417 mmol) in DMF (6 mL) was treated with tetrazole (0.45 M solution in MeCN, 6.298 mL, 2.834 mmol). After aging for 10 min. the solution of phos-phoramidite was added via syringe to the suspension of 1-ethyl-3-[6-fluoro-5-[2-(1-hydroxy-1-methyl-ethyl)pyri-midin-5-yl]-7-[(2R)-tetrahydrofuran-2-yl]-1H-benzimida-zol-2-yl]urea (23). The resulting reaction mixture was stirred for 5 hours, then cooled to 0° C. and treated with mCPBA (558.9 mg, 2.267 mmol). The resulting solution was stirred for 5 min. at 0° C., then for 30 min at 23° C. after which time the crude reaction mixture was diluted with EtOAc (100 mL) and washed successively with saturated aqueous sodium bicarbonate and brine (100 mL each), then dried (magnesium sulfate) filtered and concentrated in vacuo. The residue was purified by MPLC using an ISCO COMBIFLASH brand flash chromatography purification system (40 g column) eluting with a 0-8% EtOH in DCM linear gradient over 24 column volumes at 40 mL/min flow to give 2-cyanoethyl[1-[5-[2-(ethylcarbamoylamino)-6-fluoro-7-[(2R)-tetrahydrofuran-2-yl]-1H-benzimidazol-5-yl]pyrimidin-2-yl]-1-methyl-ethyl]hexadecyl phosphate (31) (0.89 g, 1.132 mmol, 79.89%) as a clear glassy oil. $^1$H NMR shows doubling of some peaks, due to diastereomers (stereogenic phosphate). ESMS (M+1)=786.6; $^1$H NMR (300.0 MHz, CDCl$_3$) δ 10.82 (br s, 1H), 8.91 (d, J=7.0 Hz, 2H), 7.18 (dd, J=6.0, 15.0 Hz, 1H), 5.31 (br s, 1H), 4.60-4.55 (m, 1H), 4.44-4.37 (m, 1H), 4.16 (td, J=13.3, 6.7 Hz, 3H), 3.92 (d, J=7.3 Hz, 1H), 3.34 (d, J=4.8 Hz, 2H), 3.12-2.86 (m, 2H), 2.57-2.46 (m, 1H), 2.07-1.65 (m, 11H), 1.45-1.12 (m, 31H) and 0.89 (t, J=6.0 Hz, 3H) ppm.

Example 2

Preparation of ammonium (R)-2-(5-(2-(3-ethylureido)-6-fluoro-7-(tetrahydrofuran-2-yl)-1H-benzo[d]imidazol-5-yl)pyrimidin-2-yl)propan-2-yl hexadecyl phosphate (Y)

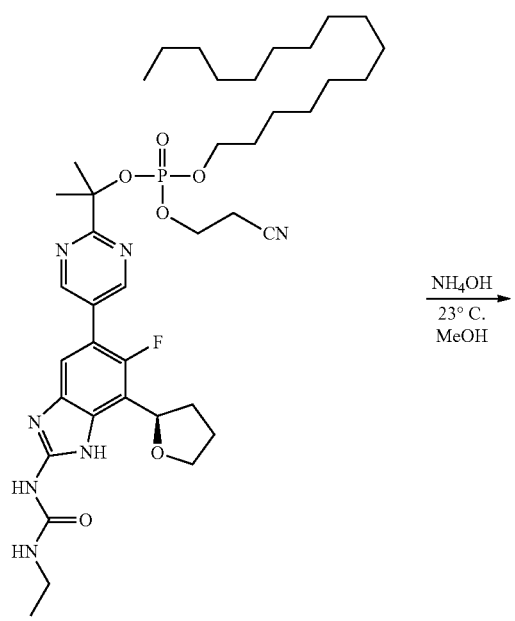

31

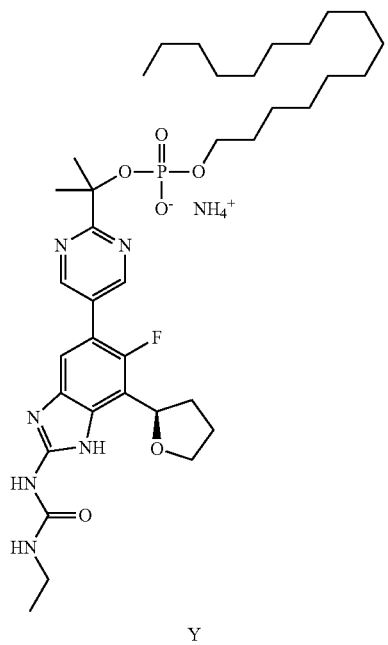

Y

To a solution of 2-cyanoethyl[1-[5-[2-(ethylcarbamoylamino)-6-fluoro-7-[(2R)-tetrahydrofuran-2-yl]-1H-benzimidazol-5-yl]pyrimidin-2-yl]-1-methyl-ethyl]hexadecyl phosphate (31) (0.89 g, 1.132 mmol) in MeOH (40 mL) at 23° C. was added ammonium hydroxide (2 mL, 51.36 mmol). After stirring for 18 hours, the reaction mixture was concentrated in vacuo. The resulting residue was purified by MPLC using an ISCO COMBIFLASH brand flash chromatography purification system (40 g silica column) eluting with 0-25% (2 M ammonia in methanol) in DCM; linear gradient over 24 column volumes at 40 mL/min flow rate. Product fractions were pooled and concentrated. The resulting residue was dissolved in 1:1 MeCN:water (20 mL), frozen and lyophilized to give ammonium (R)-2-(5-(2-(3-ethylureido)-6-fluoro-7-(tetrahydrofuran-2-yl)-1H-benzo[d]imidazol-5-yl)pyrimidin-2-yl)propan-2-yl hexadecyl phosphate (Y) (677 mg, 0.8577 mmol, 75.76%) as a white solid. ESMS (M+1)= 733.6; $^1$H NMR (300.0 MHz, CD$_3$OD) δ 8.90 (d, J=1.4 Hz, 2H), 7.36 (d, J=6.4 Hz, 1H), 5.29 (t, J=7.6 Hz, 1H), 4.24 (dd, J=6.9, 14.9 Hz, 1H), 4.00-3.86 (m, 3H), 3.35-3.28 (m, 2H), 2.50 (dd, J=6.4, 11.9 Hz, 1H), 2.13-2.03 (m, 2H), 1.90 (s, 6H), 1.84 (dd, J=3.8, 8.4 Hz, 1H), 1.62-1.53 (m, 2H), 1.34-1.19 (m, 29H) and 0.88 (t, J=6.7 Hz, 3H) ppm. Elemental Analysis Calculated for C$_{37}$H$_{61}$FN$_7$O$_6$P (corrected for 3.16% w/w water, as determined by the Karl-Fischer oven method): C, 57.39; H, 8.29; N, 12.66; F, 2.45; P, 4.00. Found: C, 57.15; H, 8.19; N, 12.27; F, 2.50; P, 4.39.

Part IV: Synthesis of Phosphate Ester Z of Formula (I)

Prodrug compound Z may be prepared from compound 23 as shown in Scheme 1 according to the following experimental procedures.

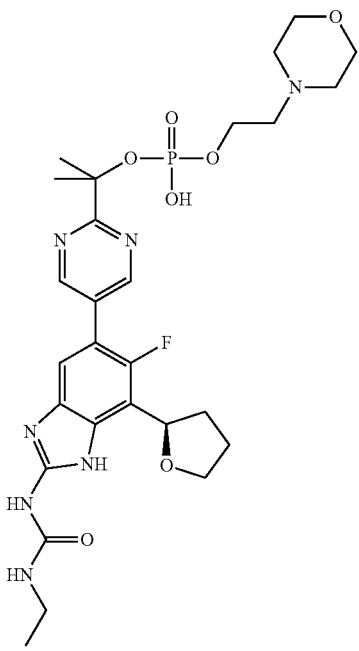

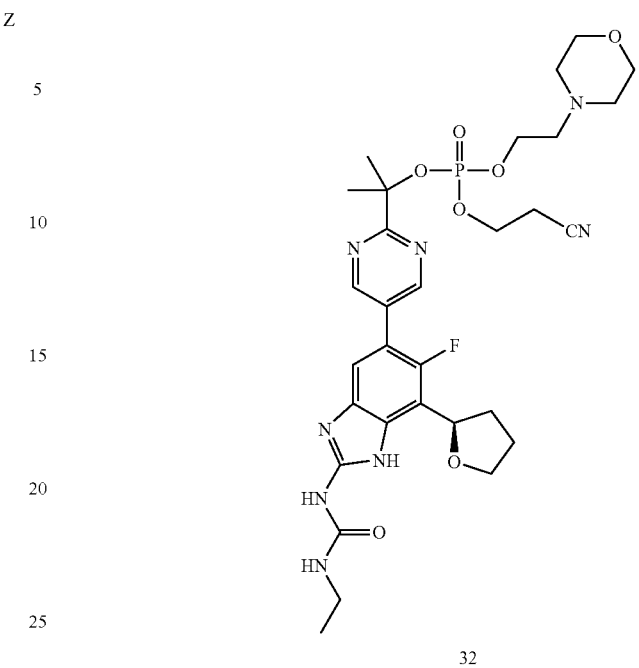

Preparation 18

Preparation of 2-cyanoethyl[1-[5-[2-(ethylcarbamoylamino)-6-fluoro-7-[(2R)-tetrahydrofuran-2-yl]-1H-benzimidazol-5-yl]pyrimidin-2-yl]-1-methyl-ethyl]2-morpholinoethyl phosphate (32)

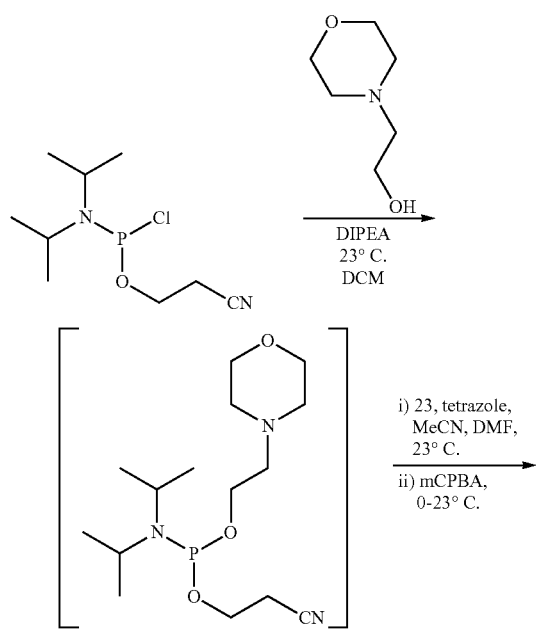

To a solution of DIPEA (366.3 mg, 493.7 µL, 2.834 mmol) in DCM (6 mL) at 23° C. under $N_2$ was added 3-[chloro-(diisopropylamino)phosphanyl]oxypropanenitrile (503.2 mg, 474.3 µL, 2.126 mmol) followed by 2-morpholinoethanol (278.9 mg, 257.5 µL, 2.126 mmol). In a separate flask under $N_2$ a suspension of (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea (23) (607 mg, 1.417 mmol) in DMF (6 mL) was treated with tetrazole solution (0.45 M in MeCN, 6.298 mL, 2.834 mmol). After aging for 10 min., the solution of phosphoramidite was added via syringe to the suspension. The resulting reaction mixture was stirred for 5 hours after which time it was cooled to 0° C., then treated with mCPBA (558.9 mg, 2.267 mmol). The resulting solution was stirred for 15 min. at 0° C., then for 30 min. at 23° C. after which time the crude reaction mixture was diluted with EtOAc (100 mL) and washed successively with saturated aqueous sodium bicarbonate and brine (100 mL each) then dried (magnesium sulfate) filtered and concentrated in vacuo. The residue was purified by MPLC using an ISCO COMBI-FLASH brand flash chromatography purification system (40 g silica column) eluting with 0-20% EtOH in DCM linear gradient over 24 CV at 40 mL/min to give 2-cyanoethyl[1-[5-[2-(ethylcarbamoylamino)-6-fluoro-7-[(2R)-tetrahydrofuran-2-yl]-1H-benzimidazol-5-yl]pyrimidin-2-yl]-1-methyl-ethyl]2-morpholinoethyl phosphate (32) (588 mg, 0.8715 mmol, 61.51%) as a clear glassy oil. $^1$H NMR shows doubling of some peaks, due to diastereomers (stereogenic phosphate). ESMS (M+1)=675.5; $^1$H NMR (300.0 MHz, $CDCl_3$) δ 10.76 (br s, 1H), 8.82 (d, J=1.0 Hz, 2H), 7.12 (dd, J=6.4, 9.7 Hz, 1H), 5.22 (br s, 1H), 4.50-4.02 (m, 5H), 3.89-3.77 (m, 1H), 3.65-3.61 (m, 4H), 3.24 (br s, 1H), 2.96-2.75

(m, 2H), 2.63 (t, J=6.0 Hz, 2H), 2.48-2.40 (m, 5H), 1.95-1.60 (m, 10H) and 1.11 (t, J=6.0 Hz, 3H) ppm.

Example 3

Preparation of 2-(5-(2-(3-ethylureido)-6-fluoro-7-((R)-tetrahydrofuran-2-yl)-1H-benzo[d]imidazol-5-yl)pyrimidin-2-yl)propan-2-yl 2-morpholinoethyl hydrogen phosphate (Z)

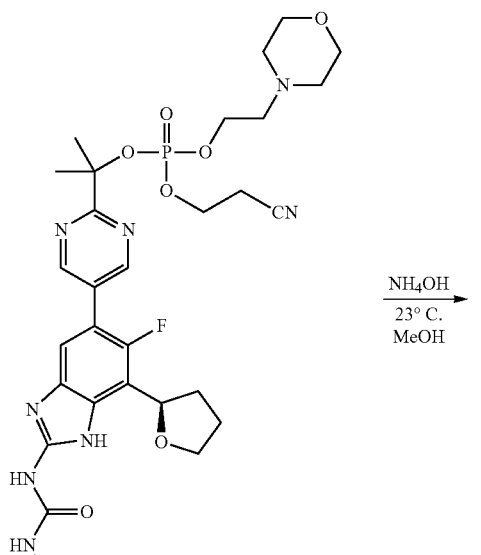

32

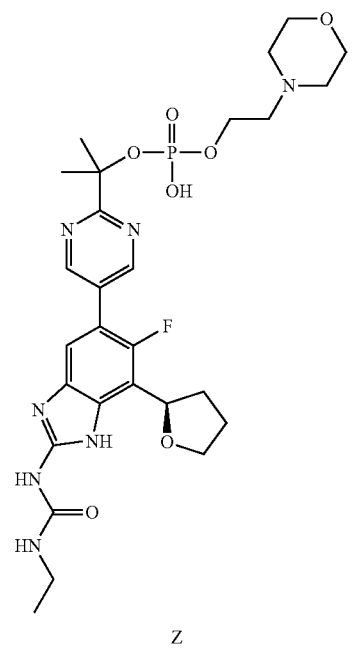

Z

To a solution of 2-cyanoethyl[1-[5-[2-(ethylcarbamoylamino)-6-fluoro-7-[(2R)-tetrahydrofuran-2-yl]-1H-benzimidazol-5-yl]pyrimidin-2-yl]-1-methyl-ethyl]2-morpholinoethyl phosphate (32) (588 mg, 0.8715 mmol) in MeOH (25 mL) at 23° C. was added ammonium hydroxide (1 mL, 25.68 mmol). After stirring for 18 hours, the reaction mixture was concentrated in vacuo. The resulting residue was dissolved in MeOH (7 mL) and purified via preparative HPLC, 7 injections using a Waters XBridge C18 5 μm OBD column (19× 100 mm) eluting with 10-90% aq MeCN with 0.1% NH$_4$OH gradient over 15 min at 20 mL/min flow rate. Product fractions were pooled, frozen and lyophilized to give 2-(5-(2-(3-ethylureido)-6-fluoro-7-((R)-tetrahydrofuran-2-yl)-1H-benzo[d]imidazol-5-yl)pyrimidin-2-yl)propan-2-yl 2-morpholinoethyl hydrogen phosphate (Z) (400 mg, 0.5998 mmol, 68.83%) as a white solid. ESMS (M+1)=622.2; $^1$H NMR (300.0 MHz, CD$_3$OD) δ 8.96-8.91 (m, 2H), 7.44 (d, J=6.5 Hz, 1H), 5.41-5.36 (m, 1H), 4.31-4.24 (m, 3H), 4.00 (dd, J=7.0, 15.0 Hz, 1H), 3.87 (br s, 4H), 3.37-3.26 (m, 4H), 2.60-2.47 (m, 1H), 2.14 (dd, J=6.6, 14.6 Hz, 2H), 1.91 (s, 6H) and 1.21 (t, J=7.2 Hz, 3H) ppm. Elemental Analysis Calculated for C$_{27}$H$_{37}$FN$_7$O$_7$P (corrected for 5.28% w/w water, as determined by the Karl-Fischer oven method): C, 49.42; H, 6.27; N, 14.94; F, 2.90; P, 4.72. Found: C, 48.87; H, 6.16; N, 14.98; F, 2.78; P, 5.05.

Part V: Enzymology Studies

The enzyme inhibition activities of selected compounds of this invention were determined in the experiments described below:

Part VA. DNA Gyrase ATPase Assay

The ATP hydrolysis activity of *S. aureus* DNA gyrase was measured by coupling the production of ADP through pyruvate kinase/lactate dehydrogenase to the oxidation of NADH. This method has been described previously (Tamura and Gellert, 1990, *J. Biol. Chem.*, 265, 21342).

ATPase assays were carried out at 30° C. in buffered solutions containing 100 mM TRIS pH 7.6, 1.5 mM MgCl$_2$, 150 mM KCl. The coupling system contains final concentrations of 2.5 mM phosphoenol pyruvate, 200 μM nicotinamide adenine dinucleotide (NADH), 1 mM DTT, 30 ug/ml pyruvate kinase, and 10 ug/ml lactate dehydrogenase. The enzyme (90 nM final concentration) and a DMSO solution (3% final concentration) of the selected compound were added. The reaction mixture was allowed to incubate for 10 minutes at 30° C. The reaction was initiated by the addition of ATP to a final concentration of 0.9 mM, and the rate of NADH disappearance was monitored at 340 nanometers over the course of 10 minutes. The K$_i$ values were determined from rate versus concentration profiles.

Selected compounds of the present invention were found to inhibit *S. aureus* DNA gyrase. Table 1 shows the inhibitory activity of these compounds in the *S. aureus* DNA gyrase inhibition assay.

TABLE 1

| Inhibition of *S. aureus* DNA Gyrase | |
|---|---|
| Selected Compound | K$_i$ (nM) |
| Compound 23 | 9 |
| Compound X | <9 |
| Compound Y | 13 |
| Compound Z | <9 |

Part VB. DNA Topo IV ATPase Assay

The conversion of ATP to ADP by *S. aureus* TopoIV enzyme was coupled to the conversion of NADH to NAD+, and the progress of the reaction was measured by the change in absorbance at 340 nm. TopoIV (64 nM) was incubated with the selected compound (3% DMSO final) in buffer for 10 minutes at 30° C. The buffer consisted of 100 mM Tris 7.5, 1.5 mM MgCl2, 200 mM K·Glutamate, 2.5 mM phosphoenol pyruvate, 0.2 mM NADH, 1 mM DTT, 5 μg/mL linearized DNA, 50 μg/mL BSA, 30 μg/mL pyruvate kinase, and 10 μg/mL lactate dehyrodgenase (LDH). The reaction was initiated with ATP, and rates were monitored continuously for 20 minutes at 30° C. on a Molecular Devices SpectraMAX plate reader. The inhibition constant, Ki, was determined from plots of rate vs. concentration of selected compound fit to the Morrison Equation for tight binding inhibitors.

Selected compounds of the present invention were found to inhibit *S. aureus* DNA Topo IV. Table 2 shows the inhibitory activity of these compounds in the *S. aureus* DNA gyrase inhibition assay.

TABLE 2

Inhibition of *S. aureus* DNA Topo IV

| Selected Compound | $K_i$ (nM) |
|---|---|
| Compound 23 | 9 |
| Compound X | 45 |
| Compound Y | 24 |
| Compound Z | 80 |

Part VI: Aqueous Solubility Study

The aqueous solubilities of compounds 23, X, Y, and Z were determined according to the following procedure.

Preparation of Samples.

Aqueous samples of each compound were prepared as follows. Compounds were weighed (20-30 mg compound) in 4 ml clear vials prior to adding water (0.5 mL) and stirring by magnetic stirrer. 1.0N HCl was added to the suspension to adjust the pH to the desired range. After stirring for 96 hours at room temperature, the suspension was filtered through a 0.22 micron filter (Millipore, Ultrafree centrifugal filters, Durapore PVDF 0.22 μm, Cat# UFC30GVNB). The filtrate was collected and the pH measured with a pH meter. The filtrates containing compounds X and Z were diluted 100-fold and 400-fold, respectively, to provide an appropriate concentration for HPLC analysis. The filtrates containing compounds 23 and Y did not require dilution.

Preparation of Standard Solutions.

Standard solutions of each compound were prepared according to the following procedure. 1 to 2 mg of each compound was accurately weighed into a 10 mL volumetric flask and either water (for compounds X and Z), methanol (for compound Y), or 1:1 methanol:0.1N HCl (for compound 23) was added to completely dissolve the compounds. Sonication was performed for compound 23 to assist with the dissolution in 1:1 methanol:0.1N HCl. When all solids dissolved, additional solvent was added to adjust the volume of each solution to 10 ml. The resulting solutions were thoroughly mixed to give the standard solutions of each compound. Each standard solution was then diluted with solvent by 2-fold, 10-fold, and 100-fold.

Solubility Analysis.

Aliquots of each sample and each standard solution were analyzed by HPLC analysis (Agilent 1100, injection volume 10 μL, wavelength 271 nm, column XTerra® Phenyl 5 μm, 4.6×50 mm, Part No. 186001144, mobile phase: A: 0.1% TFA in water 0.1% TFA in AcN). Each standard solution was injected three times, and each of the samples was injected twice. Standard curves were obtained by plotting the average of the peak area from the HPLC versus the concentrations of the standard solutions (with appropriate corrections for the weights of the standards based on total water content of the solid as determined by elemental analysis). The concentration of each sample was calculated from the peak area of the aqueous sample from the HPLC results and the slope and intercept of the standard curves. The solubility values listed in Table 3 below were derived from the product of the concentration of the sample and the dilution factor of the sample.

TABLE 3

Aqueous Solubility of Compounds 23, X, Y, and Z

| Compound | Solid form | pH | Solubility (mg/mL) |
|---|---|---|---|
| Compound 23 | crystalline | >3.0 | <0.001 |
| Compound X | crystalline | 4.41 | 12.74 |
| Compound Y | crystalline | 3.01 | <0.001 |
| Compound Z | Amorphous | 4.35 | >41 |

The invention claimed is:

1. A compound of the formula (I):

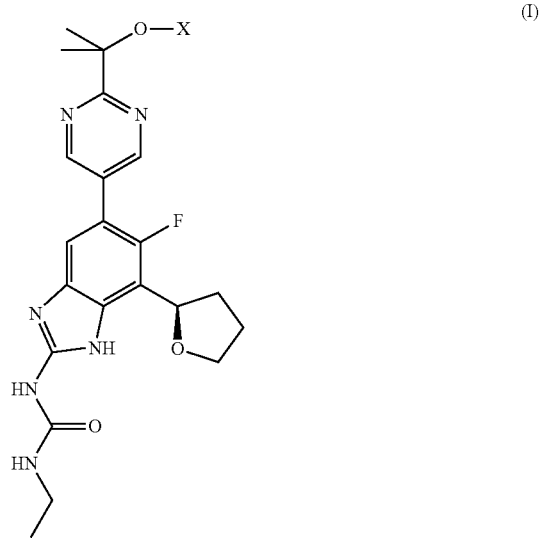

(I)

or a pharmaceutically acceptable salt thereof, wherein
X is —PO(OH)O—$R^1$, or —PO($O^-M^+$)O—$R^1$;
$M^+$ is a pharmaceutically acceptable monovalent cation;
$R^1$ is ($C_1$-$C_{20}$)-alkyl, ($C_2$-$C_{20}$)-alkenyl, —($CH_2CH_2O$)$_n$$CH_3$, or $R^2$; wherein said alkyl or alkenyl is optionally substituted with $R^2$, —$OR^9$, —$N(R^9)_2$, —CN, —C(O)$OR^9$, —C(O)N($R^9$)$_2$, —N($R^9$)—C(O)—$R^9$, halogen, —$CF_3$, or —$NO_2$;
each $R^2$ is independently a 5-6 membered carbocyclic or heterocyclic aliphatic ring system; wherein any of said heterocyclic ring systems contains one or more heteroatoms selected from O, N, and N($R^9$); and wherein any of said ring systems optionally contains 1 to 4 substituents independently selected from —OH, $C_1$-$C_4$ alkyl, and —O—($C_1$-$C_4$)-alkyl;
each $R^9$ is independently H or a $C_1$-$C_4$ alkyl group; and
n is an integer 1 to 5.

2. The compound of claim 1, wherein X is —PO($O^-M^+$)O—$R^1$; and $M^+$ is selected from a group consisting of $Li^+$, $Na^+$, $K^+$, N-methyl-D-glucamine, and N($R^9$)$_4^+$.

3. The compound of either claim 1, wherein $R^1$ is ($C_1$-$C_{20}$)-alkyl, ($C_2$-$C_{20}$)-alkenyl, or —O($CH_2CH_2O$)$_n$$CH_3$, wherein n is an integer 1, 2 or 3, morpholinoethyl, 4-ethyltetrahydro-2H-pyranyl, piperdinylethyl, piperazinylethyl, or pyrrolidinylethyl.

4. The compound of claim 3, wherein $R^1$ is morpholinoethyl, 4-ethyltetrahydro-2H-pyranyl, piperdinylethyl, piperazinylethyl, or pyrrolidinylethyl.

5. The compound of claim 3, wherein $R^1$ is $(C_1$-$C_{20})$-alkyl.

6. The compound of claim 3, wherein $R^1$ is —O(CH$_2$CH$_2$O)$_n$CH$_3$, wherein n is an integer 1, 2 or 3.

7. The compound of claim 1, wherein the compound is (R)-2-(5-(2-(3-ethylureido)-6-fluoro-7-(tetrahydrofuran-2-yl)-1H-benzo[d]imidazol-5-yl)pyrimidin-2-yl)propan-2-yl 2-(2-methoxyethoxy)ethyl hydrogen phosphate.

8. The compound of claim 1, wherein the compound is ammonium (R)-2-(5-(2-(3-ethylureido)-6-fluoro-7-(tetrahydrofuran-2-yl)-1H-benzo[d]imidazol-5-yl)pyrimidin-2-yl)propan-2-yl 2-(2-methoxyethoxy)ethyl phosphate.

9. The compound of claim 1, wherein the compound is (R)-2-(5-(2-(3-ethylureido)-6-fluoro-7-(tetrahydrofuran-2-yl)-1H-benzo[d]imidazol-5-yl)pyrimidin-2-yl)propan-2-yl hexadecyl hydrogen phosphate.

10. The compound of claim 1, wherein the compound is ammonium (R)-2-(5-(2-(3-ethylureido)-6-fluoro-7-(tetrahydrofuran-2-yl)-1H-benzo[d]imidazol-5-yl)pyrimidin-2-yl)propan-2-yl hexadecyl phosphate.

11. The compound of claim 1, wherein the compound is 2-(5-(2-(3-ethylureido)-6-fluoro-7-((R)-tetrahydrofuran-2-yl)-1H-benzo[d]imidazol-5-yl)pyrimidin-2-yl)propan-2-yl 2-morpholinoethyl hydrogen phosphate.

12. A pharmaceutical composition comprising a compound according to any of claim 1, or a pharmaceutically acceptable salt thereof, and a pharmaceutically acceptable carrier, adjuvant, or vehicle.

13. The pharmaceutical composition of claim 12, further comprising a second therapeutic agent selected from an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

14. The pharmaceutical composition of claim 12, further comprising an agent that increases the susceptibility of bacterial organisms to antibiotics.

15. A method of decreasing or inhibiting *Streptococcus pneumoniae, Staphylococcus epidermidis, Enterococcus faecalis, Enterococcus faecium, Staphylococcus aureus, Clostridium difficile, Moraxella catarrhalis, Neisseria gonorrhoeae, Neisseria meningitidis, Mycobacterium tuberculosis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci bacterial quantity in a biological sample comprising contacting said biological sample with the compound according to claim 1, or a pharmaceutically acceptable salt thereof.

16. A method for treating a bacterial infection in a patient, wherein the bacterial infection is characterized by the presence of one or more of *Streptococcus pneumoniae, Staphylococcus epidermidis, Enterococcus faecalis, Enterococcus faecium, Staphylococcus aureus, Clostridium difficile, Moraxella catarrhalis, Neisseria gonorrhoeae, Neisseria meningitidis, Mycobacterium tuberculosis, Mycobacterium avium* complex, *Mycobacterium abscessus, Mycobacterium kansasii, Mycobacterium ulcerans, Chlamydophila pneumoniae, Chlamydia trachomatis, Haemophilus influenzae Streptococcus pyogenes* or β-haemolytic streptococci, comprising administering to said patient the compound according to claim 1, or a pharmaceutically acceptable salt thereof.

17. The method of claim 16, wherein the bacterial infection is selected from one or more of the following: upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections, uncomplicated skin and skin structure infections, complicated skin and skin structure infections (cSSSI), catheter infections, pharyngitis, sinusitis, otitis externa, otitis media, bronchitis, empyema, pneumonia, community acquired pneumoniae (CAP), hospitalized acquired pneumonia, hospitalized bacterial pneumonia, diabetic foot infections, vancomycin resistant enterococci infections, cystitis and pyelonephritis, renal calculi, prostatitis, peritonitis and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

18. The method of claim 17, wherein the bacterial infection is selected from one or more of the following: community acquired pneumoniae (CAP), hospitalized acquired pneumonia, hospitalized bacterial pneumonia, bacteremia, diabetic foot infections, catheter infections, uncomplicated skin and skin structure infections, complicated skin and skin structure infections (cSSSI), vancomycin resistant enterococci infections or osteomyelitis.

19. The method of claim 16, further comprising administering to said patient an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound, either as part of a multiple dosage form together with said compound or salt or as a separate dosage form.

\* \* \* \* \*